US012802274B2

(12) United States Patent
He et al.

(10) Patent No.: US 12,802,274 B2
(45) Date of Patent: *Nov. 17, 2026

(54) APPARATUSES, SYSTEMS, AND METHODS FOR MANAGING AUTO-EXPOSURE OF IMAGE FRAMES DEPICTING SIGNAL CONTENT AGAINST A DARKENED BACKGROUND

(71) Applicant: Intuitive Surgical Operations, Inc., Sunnyvale, CA (US)

(72) Inventors: Zhen He, Cupertino, CA (US); Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 18/800,636

(22) Filed: Aug. 12, 2024

(65) Prior Publication Data

US 2024/0404110 A1 Dec. 5, 2024

Related U.S. Application Data

(63) Continuation of application No. 17/369,612, filed on Jul. 7, 2021, now Pat. No. 12,087,014.

(Continued)

(51) Int. Cl.

*G06T 7/80* (2017.01)
*A61B 1/04* (2006.01)

(Continued)

(52) U.S. Cl.

CPC ................ *G06T 7/80* (2017.01); *A61B 1/043* (2013.01); *G06T 5/20* (2013.01); *G06T 5/70* (2024.01);

(Continued)

(58) Field of Classification Search

CPC .... G06T 7/80; G06T 5/20; G06T 5/70; G06T 2207/10016; G06T 2207/10064;

(Continued)

(56) References Cited

U.S. PATENT DOCUMENTS

| | | | |
|---|---|---|---|
| 9,313,415 | B2 | 4/2016 | Schieltz |
| 2003/0078477 | A1 | 4/2003 | Kang et al. |

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Sinh Tran
*Assistant Examiner* — Angel L Garces-Rivera

(57) ABSTRACT

An illustrative apparatus may identify, within an image frame captured by an image capture system, a signal region of the image frame and a background region of the image frame; determine one or more of a signal auto-exposure value of the signal region or a background auto-exposure value of the background region; and adjust, based on one or more of the signal auto-exposure value or the background auto-exposure value, one or more auto-exposure parameters used by the image capture system to capture an additional image frame. The identifying of the signal region and the background region may include identifying pixels of the image frame that have auto-exposure values that exceed an auto-exposure value threshold to be included within the signal region, and identifying pixels of the image frame that have auto-exposure values that do not exceed the auto-exposure value threshold to be included within the background region.

19 Claims, 12 Drawing Sheets

Related U.S. Application Data

(60) Provisional application No. 63/050,531, filed on Jul. 10, 2020.

(51) Int. Cl.

| | |
|---|---|
| ***G06T 5/20*** | (2006.01) |
| ***G06T 5/70*** | (2024.01) |
| ***H04N 23/50*** | (2023.01) |
| ***H04N 23/71*** | (2023.01) |
| ***H04N 23/73*** | (2023.01) |

(52) U.S. Cl.
CPC ............. *H04N 23/71* (2023.01); *H04N 23/73* (2023.01); *G06T 2207/10016* (2013.01); *G06T 2207/10064* (2013.01); *G06T 2207/10068* (2013.01); *G06T 2207/30004* (2013.01); *H04N 23/555* (2023.01)

(58) Field of Classification Search
CPC ........... G06T 2207/10068; G06T 2207/30004; A61B 1/043; A61B 1/00009; A61B 1/045; H04N 23/71; H04N 23/73; H04N 23/555; H04N 23/74
See application file for complete search history.

(56) References Cited

U.S. PATENT DOCUMENTS

| | | | | |
|---|---|---|---|---|
| 2006/0039690 | A1 * | 2/2006 | Steinberg | G06T 7/174<br>396/155 |
| 2007/0110427 | A1 * | 5/2007 | Tsai | G03B 9/70<br>396/166 |
| 2012/0105668 | A1 * | 5/2012 | Velarde | H04N 23/71<br>348/229.1 |
| 2014/0046341 | A1 | 2/2014 | DiCarlo | |
| 2021/0110190 | A1 | 4/2021 | Park et al. | |
| 2022/0012915 | A1 | 1/2022 | He et al. | |

* cited by examiner

APPARATUSES, SYSTEMS, AND METHODS FOR MANAGING AUTO-EXPOSURE OF IMAGE FRAMES DEPICTING SIGNAL CONTENT AGAINST A DARKENED BACKGROUND

RELATED APPLICATIONS

The present application is a continuation of U.S. patent application Ser. No. 17/369,612, filed Jul. 7, 2021, which claims priority under 35 U.S.C. § 119 (e) to U.S. Provisional Patent Application No. 63/050,531, filed Jul. 10, 2020, each of which is incorporated herein by reference in its entirety.

BACKGROUND INFORMATION

While conventional auto-exposure algorithms adequately serve many types of images, images depicting content against a darkened background may have certain characteristics that render conventional auto-exposure algorithms suboptimal or inadequate in various ways. For instance, for images in which a background is dark and brighter signal content covers a relatively small portion of the overall image, conventional auto-exposure algorithms may be configured to adjust auto-exposure parameters to reach a target luminance that leaves the background areas still dark while overexposing the brighter signal content. By overexposing the image in this way, important details of the signal content as depicted in the image may be lost.

SUMMARY

The following description presents a simplified summary of one or more aspects of the apparatuses, systems, and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative apparatus for managing auto-exposure of image frames may include one or more processors and memory storing executable instructions that, when executed by the one or more processors, cause the apparatus to perform various operations described herein. For example, the apparatus may identify, within an image frame captured by an image capture system, a signal region of the image frame and a background region of the image frame. The apparatus may also determine one or more of a signal auto-exposure value of the signal region or a background auto-exposure value of the background region. Based on one or more of the signal auto-exposure value or the background auto-exposure value, the apparatus may determine a frame auto-exposure value, and based on the frame auto-exposure value, the apparatus may adjust one or more auto-exposure parameters used by the image capture system to capture an additional image frame.

An illustrative system for managing auto-exposure of image frames may include a fluorescence illumination source, an image capture device, and one or more processors. The fluorescence illumination source may be configured to illuminate tissue within a body undergoing a fluorescence-guided medical procedure. For example, a portion of the tissue may include a fluorescence imaging agent that fluoresces when illuminated by the fluorescence illumination source. The image capture device may be configured to capture an image frame sequence that includes an image frame depicting a view of the body as the tissue is illuminated by the fluorescence illumination source. The one or more processors may be configured to identify, within the image frame captured by the image capture device, (1) a signal region of the image frame associated with the portion of the tissue that includes the fluorescence imaging agent and (2) a background region of the image frame associated with a portion of the tissue that does not include the fluorescence imaging agent. The one or more processors may also be configured to determine one or more of a signal auto-exposure value of the signal region or a background auto-exposure value of the background region. Based on one or more of the signal auto-exposure value or the background auto-exposure value, the one or more processors may determine a frame auto-exposure value, and, based on the frame auto-exposure value, may adjust one or more auto-exposure parameters used by the image capture device or the fluorescence illumination source to capture an additional image frame of the image frame sequence.

An illustrative non-transitory computer-readable medium may store instructions that, when executed, cause one or more processors of a computing device to perform various operations described herein. For example, the one or more processors may identify, within an image frame captured by an image capture system, a signal region of the image frame and a background region of the image frame. The one or more processors may also determine one or more of a signal auto-exposure target of the signal region or a background auto-exposure target of the background region. Based on one or more of the signal auto-exposure target or the background auto-exposure target, the one or more processors may determine a frame auto-exposure target, and, based on the frame auto-exposure target, the one or more processors may adjust one or more auto-exposure parameters used by the image capture system to capture an additional image frame.

An illustrative method for managing auto-exposure of image frames may include various operations described herein, each of which may be performed by a computing device such as an auto-exposure management apparatus described herein. For example, the method may include identifying, within an image frame captured by an image capture system, a signal region of the image frame. The method may also include determining a signal auto-exposure value of the signal region, and determining, based on the signal auto-exposure value, a frame auto-exposure value. The method may also include adjusting, based on the frame auto-exposure value, one or more auto-exposure parameters used by the image capture system to capture an additional image frame.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
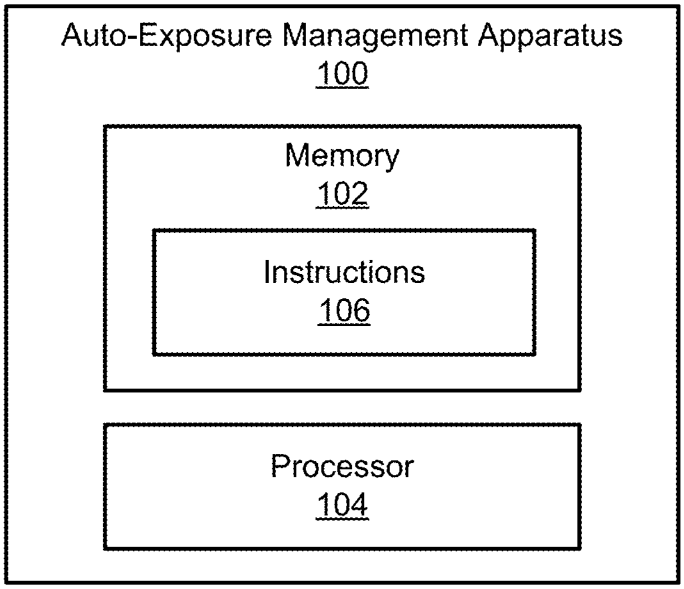
FIG. 1 shows an illustrative auto-exposure management apparatus for managing auto-exposure of image frames according to principles described herein.

Apparatuses, systems, and methods for managing auto-exposure of image frames are described herein. As mentioned above, certain signal content that is displayed against a darkened (e.g., black) background may not be well served by conventional auto-exposure algorithms. For instance, as one example of where this type of issue may come into play, an endoscopic image capture device operating in a fluorescence imaging mode will be considered. As described in more detail below, such an image capture device may facilitate a fluorescence-guided medical procedure performed by medical staff (e.g., a surgeon performing the medical procedure, staff members assisting with the medical procedure, etc.) by making it easier for the medical staff to view tissue to which a fluorescence imaging agent has been applied. For example, it may be desirable during certain stages of the medical procedure for staff members to be able to focus exclusively on tissue in which the fluorescence imaging agent has been injected and which therefore fluoresces when illuminated by a fluorescence illumination source. In such instances, imaging instrumentation used for the medical procedure may generate and provide an image frame sequence that contrasts fluorescence signal content (e.g., the tissue to which the fluorescence imaging agent has been applied) against a darkened background so as to make the signal content easy for the medical staff members to view and focus attention on.

Because so much black background is typically present in such image frames, an average luminance of these image frames will typically be low, and a conventional auto-exposure algorithm would generally attempt to brighten up the image sequence by adjusting various auto-exposure parameters of the image capture device to increase the exposure of an image sensor (e.g., by exposing the image sensor for a longer exposure time, with a wider aperture, etc.). Due to the nature of the signal content and darkened background in this imagery, however, such adjustments could overexpose the signal content of the image frame sequence, possibly resulting in detail of the images being lost or obscured.

Apparatuses, systems, and methods described herein are configured to manage auto-exposure for image frames. For example, apparatuses, systems, and methods described herein may be used to manage auto-exposure for image frames depicting signal content against a darkened background to specifically account for the unique challenges associated with these types of image frames. Auto-exposure parameters for image capture devices capturing such image frames may be adjusted by apparatuses and systems described herein in a manner that avoids the overexposure issues described above. In this way, implementations of apparatuses, systems, and/or methods described herein may successfully preserve details of the content while achieving a relatively clean background and minimizing (e.g., eliminating) noisy images when no signal content is present.

The medical procedure example introduced above involving the fluorescence imaging mode of the endoscopic image capture device will be used throughout this description to illustrate various aspects of the claimed subject matter. However, it will be understood that the endoscopic images of the fluorescence image mode are only intended as examples, and that the principles described herein may be applied, in various implementations, to any suitable types of signal content displayed against any suitable type of background (e.g., a darkened background) as may serve a particular application or use case. As a few additional examples, for instance, algorithms described herein may find application in night vision apparatuses and systems, in low-light camera operating modes, and so forth.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Apparatuses, systems, and methods described herein may provide any of the benefits mentioned above, as well as various additional and/or alternative benefits that will be described and/or made apparent below.

FIG. 1 shows an illustrative auto-exposure management apparatus 100 (apparatus 100) for managing auto-exposure of image frames according to principles described herein. Apparatus 100 may be implemented by computer resources (e.g., servers, processors, memory devices, storage devices, etc.) included within an image capture system (e.g., an endoscopic image capture device, etc.), by computer resources of a computing system associated with an image capture system (e.g., communicatively coupled to the image capture system), and/or by any other suitable computing resources as may serve a particular implementation.

As shown, apparatus 100 may include, without limitation, a memory 102 and a processor 104 selectively and communicatively coupled to one another. Memory 102 and processor 104 may each include or be implemented by computer hardware that is configured to store and/or process computer software. Various other components of computer hardware and/or software not explicitly shown in FIG. 1 may also be included within apparatus 100. In some examples, memory 102 and processor 104 may be distributed between multiple devices and/or multiple locations as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause apparatus 100 to perform any of the functionality described herein. Instructions 106 may be implemented by any suitable application, software, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 104 (e.g., when processor 104 is directed to perform operations represented by instructions 106 stored in memory 102), apparatus 100 may perform various functions associated with managing auto-exposure of image frames depicting signal content against a darkened background.

Figure 2:
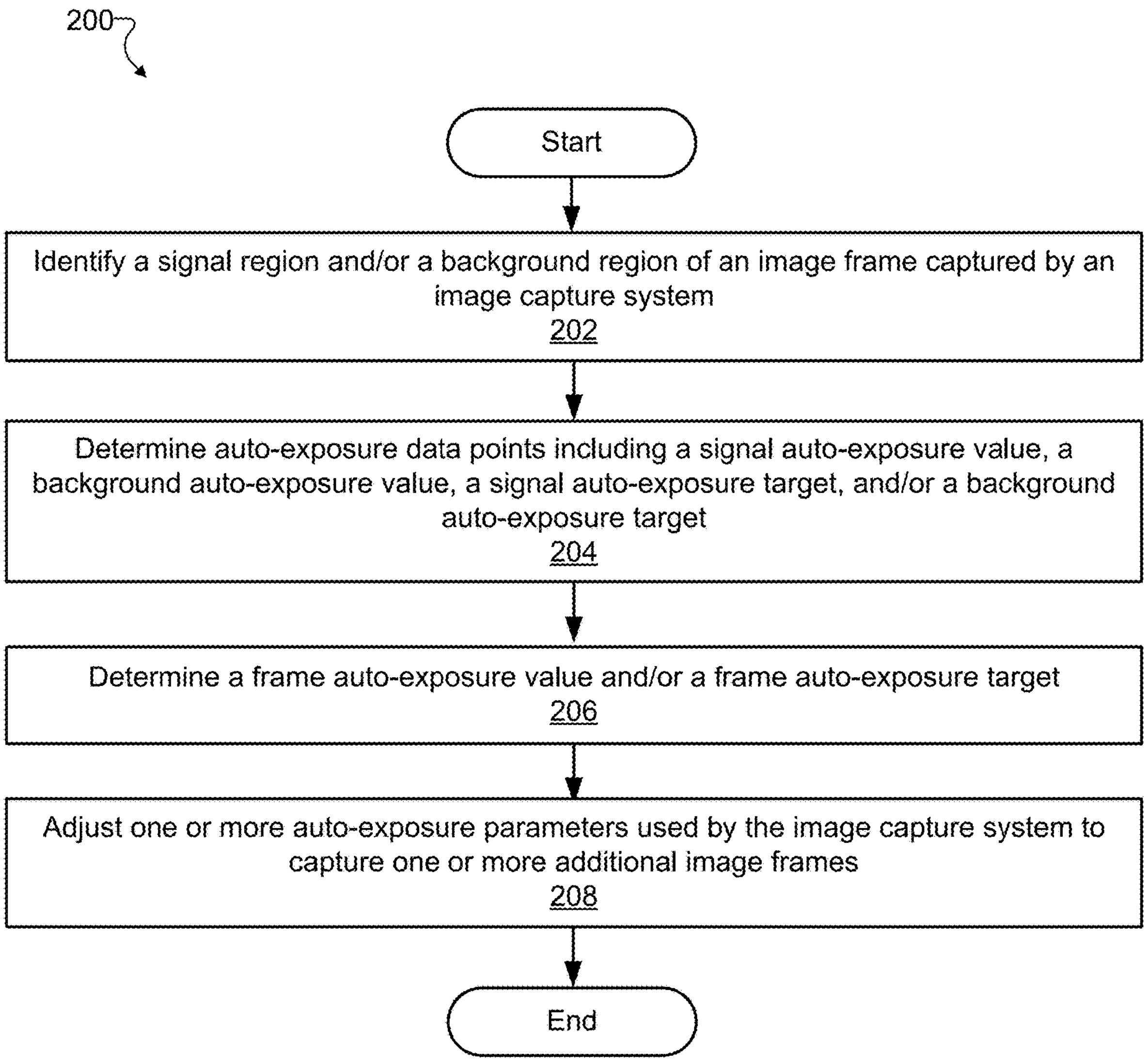
FIG. 2 shows an illustrative auto-exposure management method for managing auto-exposure of image frames according to principles described herein.

To illustrate, FIG. 2 shows an example of an auto-exposure management method 200 (method 200) that apparatus 100 may perform. While FIG. 2 illustrates illustrative operations according to one embodiment, other embodiments may omit, add to, reorder, and/or modify any of the operations shown in FIG. 2. One or more of the operations shown in FIG. 2 may be performed by an auto-exposure management apparatus (e.g., apparatus 100), an auto-exposure management system (e.g., an implementation of an auto-exposure management system described below), and/or any implementation thereof.

In operation 202, apparatus 100 may identify, within an image frame captured by an image capture system, a signal region of the image frame and/or a background region of the image frame. Referring to the fluorescent imaging example described above, for example, the image frame may depict a darkened background over which is displayed tissue that is fluorescing under a fluorescence illumination source due to a presence of a fluorescence imaging agent (e.g., a fluorescence imaging dye, etc.) injected into or otherwise applied to the tissue. In this example, apparatus 100 may identify the signal region to include those parts of the tissue that are visible in the image frame due to the fluorescing of the tissue, and may identify the background region as the areas of darkened background where fluorescence is not visible or is below a threshold level.

In operation 204, apparatus 100 may determine one or more auto-exposure data points for the signal region and/or the background region identified in operation 202. For example, based on the identification of the signal and background regions at operation 202, apparatus 100 may determine an auto-exposure value of the signal region (hereafter, a signal auto-exposure value), an auto-exposure value of the background region (hereafter, a background auto-exposure value), an auto-exposure target of the signal region (hereafter, a signal auto-exposure target), an auto-exposure target of the background region (hereafter, a background auto-exposure target), and/or any other such auto-exposure data point or property as may serve a particular implementation.

An auto-exposure value will be understood to represent certain auto-exposure-related characteristics (e.g., luminance, signal intensity, chrominance, etc.) of a particular image frame or portion thereof (e.g., region, pixel, group of pixels, etc.). For example, such characteristics may be detected by analyzing the image frame captured by the image capture system. A signal auto-exposure value may refer to an average luminance determined for pixels of the signal region of the image frame as identified by apparatus 100 at operation 202. As another example, a background auto-exposure value may refer to an average luminance determined for pixels of the background region of the image frame as identified by apparatus 100 at operation 202. In any such example, it will be understood that the average luminance (and/or one or more other average exposure-related characteristics in certain examples) referred to by an auto-exposure value may be determined as any type of average as may serve a particular implementation. For instance, an auto-exposure value may refer to a mean luminance of an image frame or portion thereof, determined by summing respective luminance values for each pixel or pixel group of the frame or region and then dividing the sum by the total number of values. As another example, an auto-exposure value may refer to a median luminance of the image frame or portion thereof, determined as the central luminance value when all the respective luminance values for each pixel or pixel group of the frame or region are ordered by value. As yet another example, an auto-exposure value may refer to a mode luminance of the image frame or portion thereof, determined as whichever luminance value, of all the respective luminance values for each pixel or pixel group of the image frame or portion, is most prevalent or repeated most often. In other examples, other types of averages (besides mean, median, or mode) and other types of exposure-related characteristics (besides luminance) may also be used to determine an auto-exposure value in any manner as may serve a particular implementation.

An auto-exposure target will be understood to refer to a target (e.g., a goal, a desirable value, an ideal, an optimal value, etc.) for the auto-exposure value of a particular image frame or portion thereof (e.g., region, pixel, pixel group, etc.). Apparatus 100 may determine the auto-exposure target, based on the particular circumstances and any suitable criteria, for the auto-exposure-related characteristics represented by the auto-exposure values. For example, auto-exposure targets may be determined at desirable levels of luminance (or other exposure-related characteristics) such as a luminance level associated with middle gray or the like. As such, a signal auto-exposure target may refer to a desired target luminance determined for pixels of the signal region of the image frame as identified by apparatus 100 at operation 202. As another example, a background auto-exposure target may refer to a desired target luminance determined for pixels of the background region of the image frame as identified by apparatus 100 at operation 202. In some examples, an auto-exposure target for a particular image frame or region may be determined as an average of the respective auto-exposure targets of pixels or pixel groups included within that image frame or region. For example, similarly as described above in relation to how auto-exposure values may be averaged, a mean, median, mode, or other suitable type of auto-exposure target average may be computed to determine an auto-exposure target for an image frame or region thereof (e.g., a signal region, a background region, etc.).

In operation 206, the auto-exposure management apparatus may determine a frame auto-exposure value and/or a frame auto-exposure target. For example, based on auto-exposure data points determined at operation 204 (e.g., based on one or more of a signal auto-exposure value, a background auto-exposure value, a signal auto-exposure target, or a background auto-exposure target), apparatus 100 may determine an auto-exposure value for the image frame (hereafter, a frame auto-exposure value) and/or an auto-exposure target for the image frame (hereafter, a frame auto-exposure target). For example, the apparatus 100 may determine an auto-exposure value for the entire image frame and/or an auto-exposure target for the entire image frame. Just as a signal auto-exposure value and a signal auto-exposure target correspond to the identified signal region of the image frame and a background auto-exposure value and a background auto-exposure target correspond to the identified background region of the image frame, a frame auto-exposure value and a frame auto-exposure target will be understood to correspond to the image frame (e.g., the image frame as a whole). As will be described in more detail below, apparatus 100 may determine the frame auto-exposure value and/or the frame auto-exposure target based on some or all of the signal and background auto-exposure values and auto-exposure targets.

In operation 208, the auto-exposure management apparatus may adjust one or more auto-exposure parameters used by the image capture system to capture one or more additional image frames. For example, once apparatus 100 has determined a frame auto-exposure value and/or a frame auto-exposure target for the image frame, apparatus 100 may adjust one or more auto-exposure parameters used by the image capture system based on the frame auto-exposure value and/or the frame auto-exposure target. In this way, the image capture system may capture one or more additional image frames (e.g., subsequent image frames in an image frame sequence being captured) using auto-exposure parameters (e.g., exposure time parameters, shutter aperture parameters, illumination intensity parameters, image signal analog and/or digital gains, etc.) that are likely to reduce the difference between auto-exposure values detected for those additional image frames and auto-exposure targets desirable for those additional image frames. Accordingly, the additional image frames are likely to be captured with more optimal exposure characteristics than might be captured without such adjustments, and users of apparatus 100 are likely to experience a superior image (e.g., an image that shows details at an optimal brightness level, etc.).

Apparatus 100 may be implemented by one or more computing devices or by computing resources of a general purpose or special purpose computing system such as will be described in more detail below. In certain embodiments, the one or more computing devices or computing resources implementing apparatus 100 may be communicatively coupled with other components such as an image capture system used to capture the image frames that apparatus 100 is configured to process. In other embodiments, apparatus 100 may be included within (e.g., implemented as a part of) an auto-exposure management system. Such an auto-exposure management system may be configured to perform all the same functions described herein to be performed by apparatus 100 (e.g., including the operations of method 200, described above), but may further incorporate additional components such as the image capture system so as to also be able to perform the functionality associated with these additional components.

Figure 3:
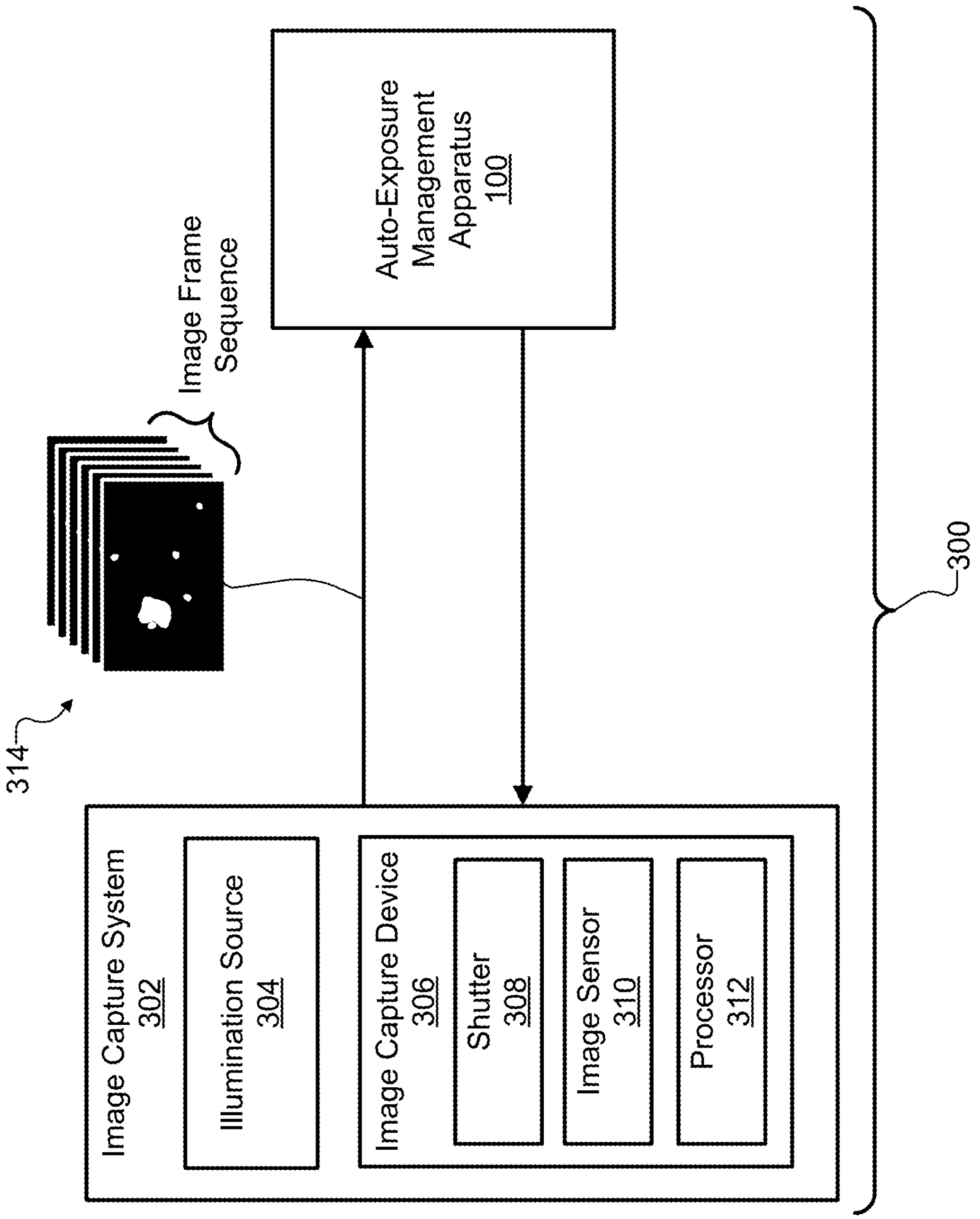
FIG. 3 shows an illustrative auto-exposure management system for managing auto-exposure of image frames according to principles described herein.

FIG. 3 shows an illustrative auto-exposure management system 300 (system 300) for managing auto-exposure of image frames. As shown, system 300 may include an implementation of apparatus 100 together with an image capture system 302 that includes an illumination source 304 and an image capture device 306 that incorporates a shutter 308, an image sensor 310, and a processor 312 (e.g., one or more image signal processors implementing an image signal processing pipeline). Within system 300, apparatus 100 and image capture system 302 may be communicatively coupled to allow apparatus 100 to direct image capture system 302 in accordance with operations described herein, as well as to allow image capture system 302 to capture and provide an image frame sequence 314 and/or other suitable captured image data. Image capture system 302 will now be described.

Illumination source 304 may be implemented by any type of source of illumination (e.g., visible light, fluorescence excitation light such as near infrared light, etc.) and may be configured to interoperate with image capture device 306 within image capture system 302. For example, illumination source 304 may provide a certain amount of illumination to a scene to facilitate image capture device 306 in capturing optimally illuminated images of the scene. As has been mentioned, while principles described herein may be applied to a wide variety of imaging scenarios, many examples explicitly described herein relate to medical procedures (e.g., fluorescence-guided medical procedures) performed using a computer-assisted medical system such as will be described in more detail below in relation to FIG. 11. In such examples, the scene for which images are being captured may include a surgical area associated with a body on which the medical procedure is being performed (e.g., a body of a live animal, a human or animal cadaver, a portion of human or animal anatomy, tissue removed from human or animal anatomies, non-tissue work pieces, training models, etc.), and system 300 or certain components thereof (e.g., image capture system 302) may be integrated with (e.g., implemented by imaging and computing resources of) a computer-assisted medical system. In examples involving a fluorescence-guided medical procedure, illumination source 304 may include a fluorescence illumination (e.g., excitation) source configured to illuminate tissue within the body undergoing the fluorescence-guided medical procedure. A portion of the tissue may include (e.g., may be injected with) a fluorescence imaging agent that fluoresces when illuminated by the fluorescence illumination source.

Image capture device 306 may be implemented by any suitable camera or other device configured to capture images of a scene. For instance, in a medical procedure example, image capture device 306 may be implemented by an endoscopic imaging device configured to capture image frame sequence 314, which may include an image frame depicting a view of the body as the tissue is illuminated by the fluorescence illumination source implemented by illumination source 304. As shown, image capture device 306 may include components such as shutter 308, image sensor 310, and processor 312.

Image sensor 310 may be implemented by any suitable image sensor, such as a charge coupled device ("CCD") image sensor, a complementary metal-oxide semiconductor ("CMOS") image sensor, or the like.

Shutter 308 may interoperate with image sensor 310 to assist with the capture and detection of light from the scene. For example, shutter 308 may be configured to expose image sensor 310 to a certain amount of light for each image frame captured. Shutter 308 may comprise an electronic shutter and/or a mechanical shutter. Shutter 308 may control how much light image sensor 310 is exposed to by opening to a certain aperture size defined by a shutter aperture parameter and/or for a specified amount of time defined by an exposure time parameter. As will be described in more detail below, these shutter-related parameters may be included among the auto-exposure parameters that apparatus 100 is configured to adjust.

Processor 312 may be implemented by one or more image signal processors configured to implement at least part of an image signal processing pipeline. Processor 312 may process auto-exposure statistics input (e.g., by tapping the signal in the middle of the pipeline to detect and process various auto-exposure data points and/or other statistics), perform optics artifact correction for data captured by image sensor 310 (e.g., by reducing fixed pattern noise, correcting defective pixels, correcting lens shading issues, etc.), perform signal reconstruction operations (e.g., white balance operations, demosaic and color correction operations, etc.), apply image signal analog and/or digital gains, and/or perform any other functions as may serve a particular implementation. Various auto-exposure parameters may dictate how the functionality of processor 312 is to be performed. For example, auto-exposure parameters may be set to define the analog and/or digital gains processor 312 applies, as will be described in more detail below.

In some examples, an endoscopic implementation of image capture device 306 may include a stereoscopic endoscope that includes two full sets of image capture components (e.g., two shutters 308, two image sensors 310, etc.) to accommodate stereoscopic differences presented to the two eyes (e.g., left eye and right eye) of a viewer of the captured image frames. Conversely, in other examples, an endoscopic implementation of image capture device 306 may include a monoscopic endoscope with a single shutter 308, a single image sensor 310, and so forth.

Apparatus 100 may be configured to control various auto-exposure parameters of image capture system 302 and may adjust such auto-exposure parameters in real time based on incoming image data captured by image capture system 302. As mentioned above, certain auto-exposure parameters of image capture system 302 may be associated with shutter 308 and/or image sensor 310. For example, apparatus 100 may direct shutter 308 in accordance with an exposure time parameter corresponding to how long the shutter is to allow image sensor 310 to be exposed to the scene, a shutter aperture parameter corresponding to an aperture size of the shutter, or any other suitable auto-exposure parameters associated with the shutter. Other auto-exposure parameters may be associated with aspects of image capture system 302 or the image capture process unrelated to shutter 308 and/or sensor 310. For example, apparatus 100 may adjust an illumination intensity parameter of illumination source 304 that corresponds to an intensity of illumination provided by illumination source 304, an illumination duration parameter corresponding to a time period during which illumination is provided by illumination source 304, or the like. As yet another example, apparatus 100 may adjust gain parameters corresponding to one or more analog and/or digital gains (e.g., analog gains, bayer gains, RGB gains, etc.) applied by processor 312 to luminance data generated by image sensor 310.

Any of these or other suitable parameters, or any combination thereof, may be updated and/or otherwise adjusted by apparatus 100 for subsequent image frames based on an analysis of the current image frame. For instance, in one example where the frame auto-exposure gain (e.g., the frame auto-exposure target divided by the frame auto-exposure value) is determined to be 6.0, various auto-exposure parameters could be set as follows: 1) a current illumination intensity parameter may be set to 100% (e.g., maximum output); 2) an exposure time parameter may be set to $1/60^{th}$ of a second (e.g., 60 fps); 3) an analog gain may be set to 5.0 (with a cap of 10.0); 4) a bayer gain may be set to 1.0 (with a cap of 3.0); and 5) an RGB gain may be set to 2.0 (with a cap of 2.0). With these settings, the gain is distributed across the analog gain (10.0/5.0=2.0), bayer gain (3.0/1.0=3.0), and RGB gain (2.0/2.0=1.0) to establish the desired 6.0 total auto-exposure gain (3.0*2.0*1.0=6.0) for the frame.

In certain examples, image capture system 302 may employ a fluorescence imaging mode to generate image frame sequence 314 in a manner that emphasizes signal content associated with fluorescing tissue by displaying the fluorescence signal content against a darkened background such as a black background.

Figure 4A:
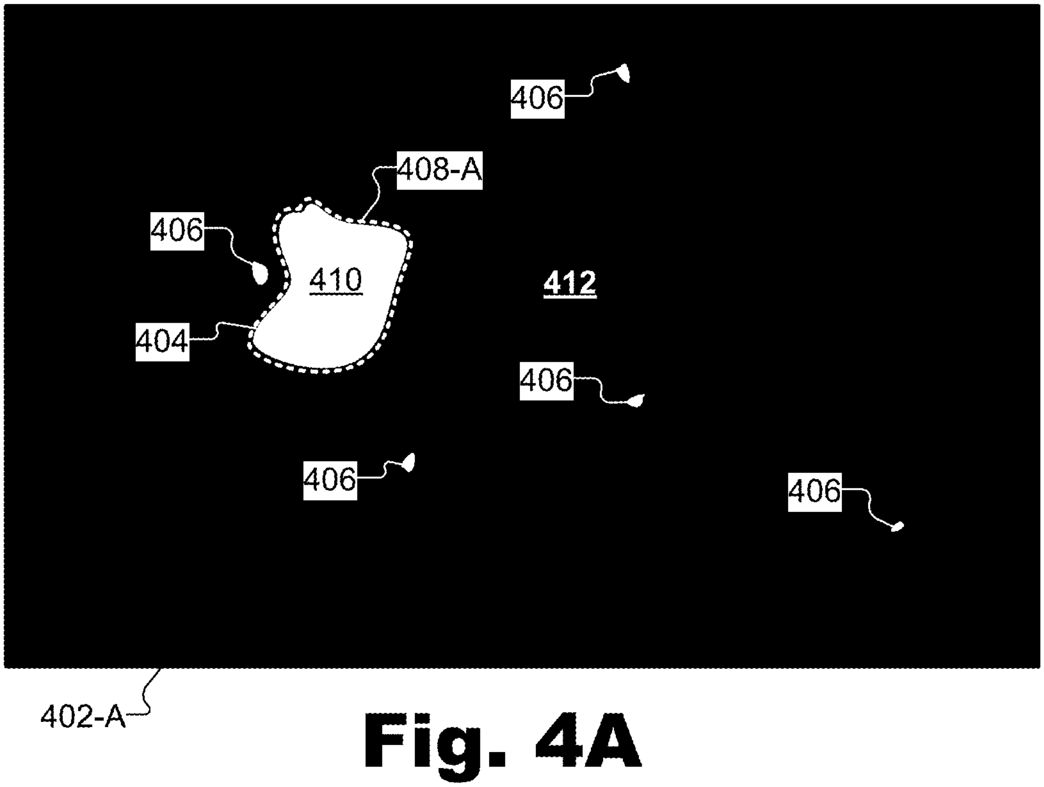
FIGS. 4A and 4B show illustrative image frames according to principles described herein.
Figure 4B:
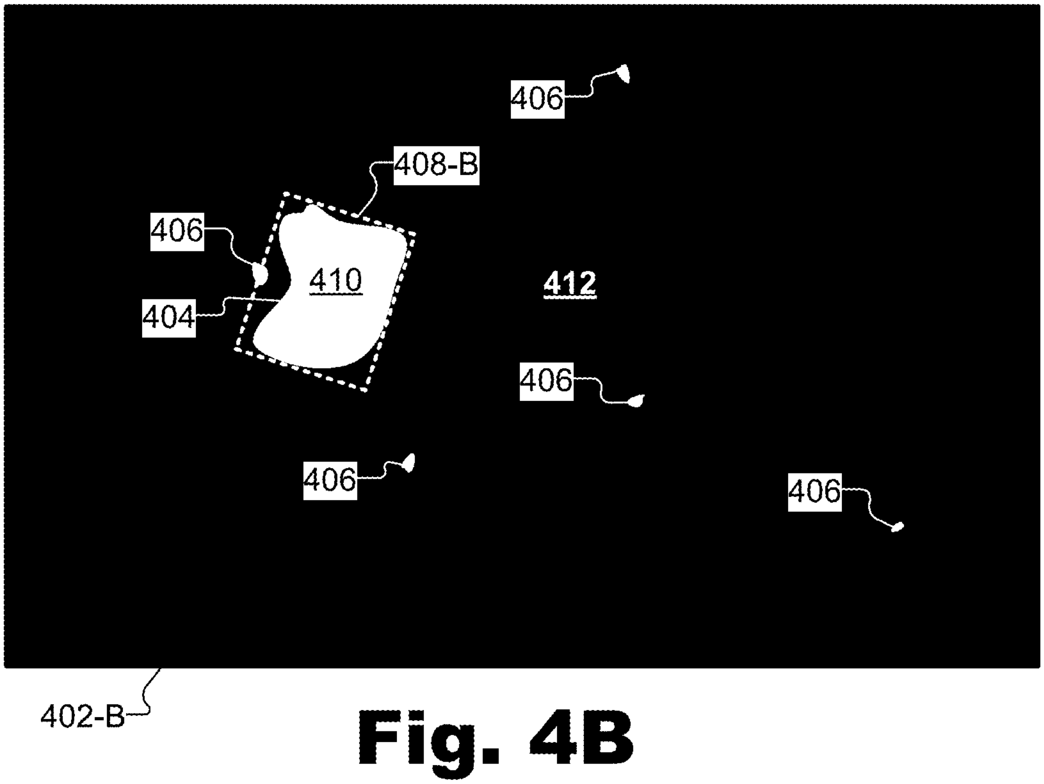

FIGS. 4A and 4B show examples of image frames 402 (e.g., image frame 402-A in FIG. 4A and image frame 402-B in FIG. 4B) that depict signal content against a darkened background and that will be understood to represent examples of an individual image frame from an image frame sequence such as image frame sequence 314 of in FIG. 3. As shown in FIG. 4A, signal content 404 and noise 406 are shown against a darkened background (e.g., the blackness upon which the white signal content 404 and noise 406 is shown). A boundary 408 (e.g., boundary 408-A or 408-B) is shown to be drawn around a signal region 410 to distinguish signal region 410 from a background region 412 in each image frame 402. Specifically, as shown in FIG. 4A, boundary 408-A is shown in this example to be closely tailored to signal content 404 such that none of the darkened background and/or noise 406 is included within signal region 410. In contrast, while FIG. 4B shows most of the same elements as FIG. 4A, the example of FIG. 4B is shown to implement a boundary 408-B that also distinguishes signal region 410 from background region 412, but that is not as closely tailored to signal content 404. As a result, FIG. 4B shows that at least some of the darkened background and/or some of noise 406 may be included within signal region 410 (as denoted by boundary 408-B). In this way, boundary 408-B may be implemented as a more regular shape (e.g., a rectangle such as shown in FIG. 4B or another regular geometric shape), which may result in certain processing efficiencies. While FIGS. 4A and 4B each show a single signal region 410, it is understood that the image frame 402 may include multiple signal regions, and the multiple signal regions may be separated in the image frame 402 by the background region 412.

In any case, it will be understood that signal region 410 may be identified so as to include (e.g., either exclusively or nearly exclusively) portions of the image frame 402 corresponding to signal content 404, while background region 412 may be identified so as to include (e.g., either exclusively or nearly exclusively) the darkened background portions of the image frame 402. It will be understood that noise 406 may be identified to be part of either signal region 410 or background region 412, as may serve a particular implementation. As one example, if noise 406 is within a threshold distance of signal region 410, the noise may be identified to be part of signal region 410. Conversely, if the noise is not within the threshold distance, the noise may be identified to be part of background region 412. As another example, if pixels associated with noise 406 have auto-exposure values that exceed a particular auto-exposure value threshold (e.g., an auto-exposure value threshold used to distinguish the signal and background regions as will be described in more detail below, or another suitable auto-exposure value threshold), the noise 406 may be identified to be part of signal region 410. Conversely, if the pixel auto-exposure values do not exceed the particular auto-exposure value threshold, the noise may be identified to be part of background region 412.

In some examples, image frames such as image frames 402 may depict, against the darkened background, fluorescence content that is generated by a fluorescence imaging agent (e.g., indocyanine green (ICG), etc.) injected into tissue so as to make the tissue fluoresce when illuminated (e.g., excited) by a fluorescence illumination source. For example, an image capture system that includes an endoscopic image capture device may capture image frames like image frames 402 as part of an image frame sequence that depicts a view of a body undergoing a fluorescence-guided medical procedure. The endoscopic image capture device may capture these image frames while operating in a fluorescence imaging mode configured to facilitate viewing the tissue to which the fluorescence imaging agent has been applied. For instance, in the fluorescence image mode, only fluorescing tissue may be visible while other areas that are not emitting fluorescence light (e.g., other anatomy surrounding the injected tissue, instrumentation and/or other objects, etc.) may remain dark.

In examples where image frames 402 depict this type of imagery, signal region 410 may correspond to the fluorescence content (e.g., the injected tissue fluorescing due to the presence of the fluorescing imaging agent), and background region 412 may correspond to the darkened background (e.g., portions of the body and/or other objects and instrumentation at the scene not having the fluorescence imaging agent). In other examples, image frames 402 may represent other types of signal content against other types of darkened backgrounds (e.g., signal content and backgrounds unrelated to fluorescence imaging or medical procedures), or any other type of image as may be served by apparatuses, systems, and/or methods described herein.

Figure 5:
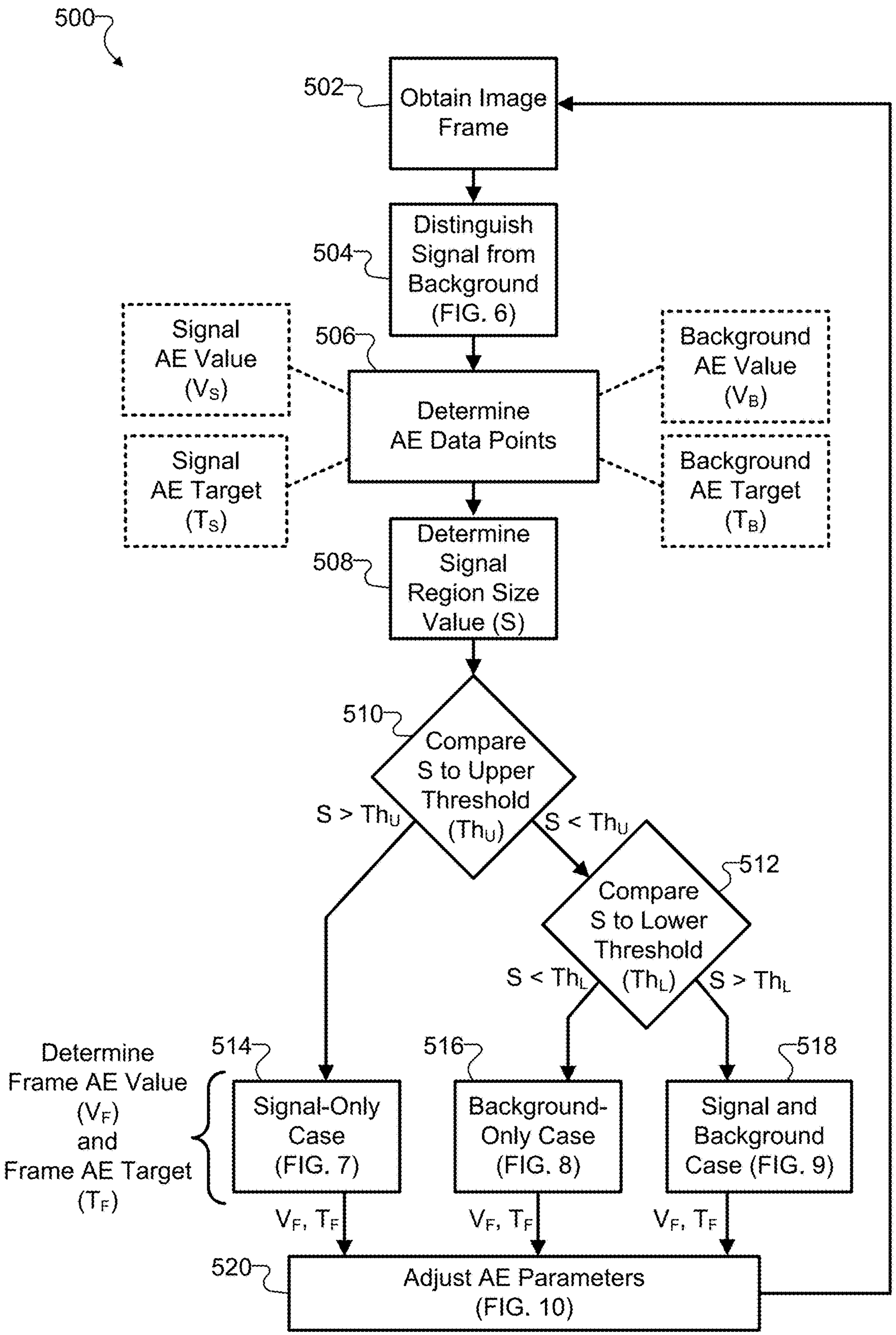
FIG. 5 shows an illustrative flow diagram for managing auto-exposure of image frames according to principles described herein.

FIG. 5 shows an illustrative flow diagram 500 for managing auto-exposure of image frames using, for example, an implementation of apparatus 100, method 200, and/or system 300. As shown, flow diagram 500 illustrates various operations 502-520, which will each be described in more detail below. It will be understood that operations 502-520 represent one embodiment, and that other embodiments may omit, add to, reorder, and/or modify any of these operations. As will be described, various operations 502-520 of flow diagram 500 may be performed for one image frame or multiple image frames (e.g., each image frame) in an image frame sequence. It will be understood that, depending on various conditions, not every operation might be performed for every frame, and the combination and/or order of operations performed from frame to frame in the image frame sequence may vary.

As illustrated by flow diagram 500, operation 502 involves obtaining an image frame, such as an image frame captured by an image capture system. As previously explained, the image frame may be a fluorescence image frame, a visible light image frame, and/or a combination thereof. Operation 504 involves distinguishing signal content from background information (e.g., a darkened background on which the signal content is displayed), such as by identifying a signal region and a background region of the image frame. Specific details for an illustrative way of performing operation 504 will be described in relation to FIG. 6. Operation 506 involves determining auto-exposure data points such as a signal auto-exposure value, a signal auto-exposure target, a background auto-exposure value, and/or a background auto-exposure target. Operation 508 involves determining a signal region size value representative of a size of the signal region within the image frame. The signal region size may be compared to one or more size thresholds. For example, in operation 510, the signal region size value may be compared to an upper threshold. For certain frames, the signal region size value may be compared to a lower threshold in operation 512. Comparing the signal region size to one or more thresholds may be used calculate a frame auto-exposure value and/or a frame auto-exposure target for the image frame. For example, in a first potential scenario (signal-only case) represented by operation 514, the signal auto-exposure value and target may be used to generate the frame auto-exposure value and target. The background auto-exposure value and target might not be used in the signal-only case. This signal-only case will be described in relation to FIG. 7. In a second potential scenario (background-only case) represented by operation 516, the background auto-exposure value and target may be used to generate the frame auto-exposure value and target. The signal auto-exposure value and target might not be used in the background-only case. This background-only case will be described in relation to FIG. 8. In a third potential scenario (signal and background case) represented by operation 518, auto-exposure datapoints related to both the signal region and the background region may be used to generate the frame auto-exposure value and target. This signal and background case will be described in relation to FIG. 9. Once the frame auto-exposure value and target are determined by one of operations 514-518, one or more auto-exposure parameters may be adjusted in operation 520. Specific details for an illustrative way of performing operation 520 will be described in relation to FIG. 10.

After operation 520 has been performed, the current image frame may be considered fully processed by the auto-exposure management apparatus or system and flow may return to operation 502, where a subsequent image frame of the image frame sequence may be obtained to repeat the process. It will be understood that, in certain examples, every image frame may be analyzed in accordance with flow diagram 500 to keep the auto-exposure data points and parameters as up-to-date as possible. In other examples, only certain image frames (e.g., every other image frame, every third image frame, etc.) may be so analyzed to conserve processing bandwidth in scenarios where more periodic auto-exposure processing still allows design specifications and targets to be achieved. It will also be understood that auto-exposure effects may tend to lag a few frames behind luminance changes at a scene, since auto-exposure parameter adjustments made based on one particular frame do not affect the exposure of that frame, but rather affect subsequent frames. Each of operations 502 through 520 will now be described in more detail with reference to aspects illustrated by FIGS. 5-10.

At operation 502, apparatus 100 may obtain an image frame (e.g., an image frame featuring signal content against a darkened background such as one of image frames 402 described above) in any manner as may serve a particular implementation. For instance, apparatus 100 may receive the image frame from image capture system 302.

At operation 504, apparatus 100 may distinguish a signal region in the obtained image frame from a background region in the obtained image frame. For example, if the image frame obtained at operation 502 is one of image frames 402-A or 402-B, apparatus 100 may distinguish signal region 410 (e.g., either the region outlined by boundary 408-A or 408-B or another suitable boundary, depending on the implementation) from background region 412, as described above in relation to FIGS. 4A-4B.

For example, apparatus 100 may distinguish the signal region from the background region by identifying a signal region and a background region within the image frame. Identifying the signal region and the background region may include comparing auto-exposure values of pixels of the image frame to an auto-exposure value threshold, and, based on the comparing, (1) identifying pixels of the image frame that have auto-exposure values that exceed the auto-exposure value threshold to be included within the signal region, and (2) identifying pixels of the image frame that have auto-exposure values that do not exceed the auto-exposure value threshold to be included within the background region.

Figure 6:
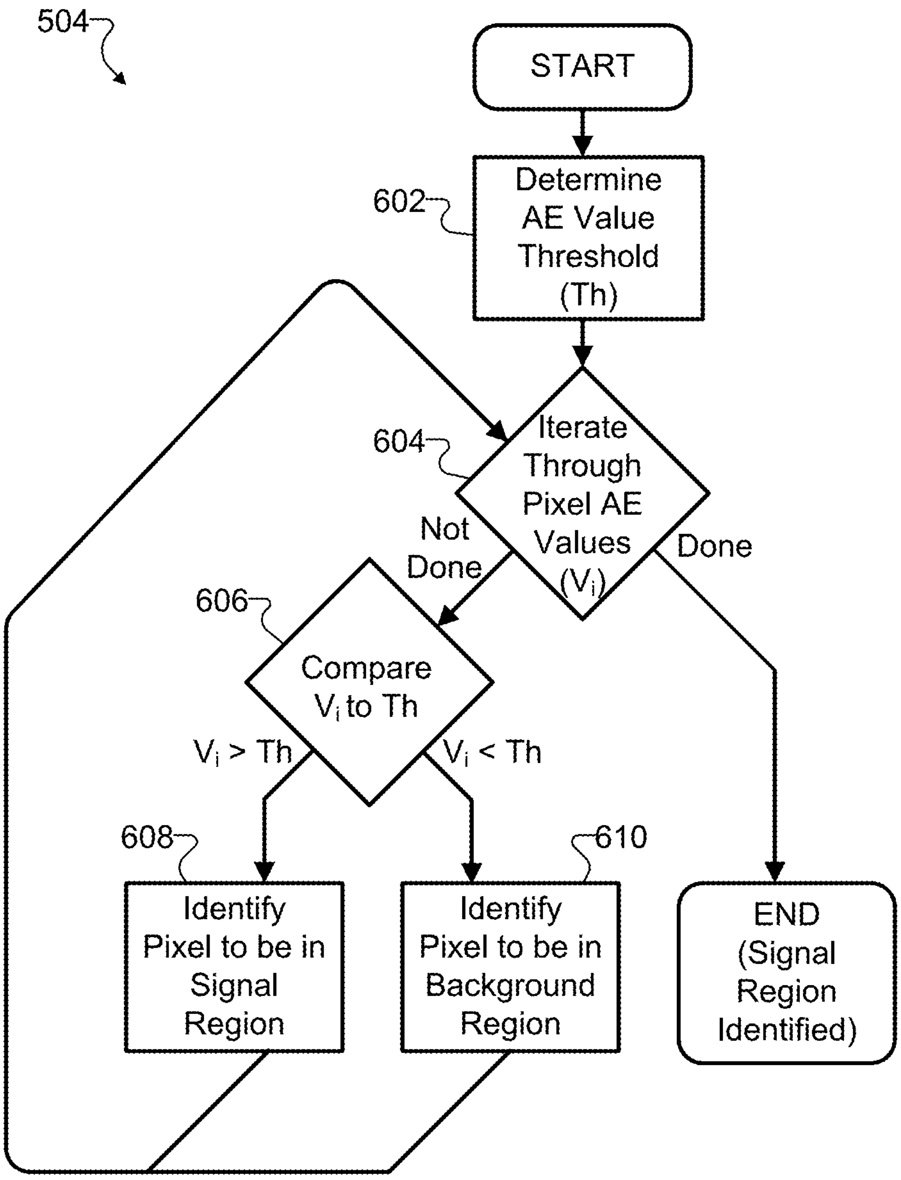
FIG. 6 shows an illustrative flow diagram for identifying a signal region and a background region within an image frame according to principles described herein.

To illustrate, FIG. 6 shows a plurality of operations 602-610 that may be performed between when operation 504 begins (labeled START) and when operation 504 is complete and the signal region and background regions are identified (labeled END). In particular, in operation 602, apparatus 100 may determine an auto-exposure value threshold (Th). The auto-exposure value threshold may be determined in any suitable way. For example, the auto-exposure value threshold may be a frame-specific dynamic value. A frame-specific dynamic threshold value may be determined based on analog and/or digital gains that have been determined for the current image frame based on the auto-exposure values and targets of one or more previous frames in the frame sequence. The determination of the auto-exposure value threshold may additionally or alternatively be based on a baseline auto-exposure value threshold that is calibrated offline with a baseline set of auto-exposure parameters. For example, prior to apparatus 100 beginning to perform the operations of flow diagram 500, auto-exposure parameters of the image capture system may be set to expose an image sensor for a particular exposure time (e.g., sixty frames per second (60 fps)) with a relatively bright illumination (e.g., full illumination of the illumination source of the image capture system) and standard gain parameters (e.g., a 1× analog gain, a 1× digital gain, etc.). With these auto-exposure parameters, a baseline auto-exposure value threshold may be determined that can be used during system operation (e.g., when the auto-exposure parameters are set to different levels). For example, during operation, apparatus 100 may dynamically determine the auto-exposure value threshold by linearly scaling this baseline threshold with one or more frame auto-exposure gains associated with the current image frame. For instance, the scaling may be performed using a current frame analog gain (e.g., an analog gain applied at an image sensor level), a current frame Bayer gain (e.g., a digital gain applied at a pipeline level) or another suitable gain.

In operation 604, apparatus 100 may iterate through each pixel of an image frame or portion of an image frame (or each cell or group of pixels in implementations that may operate on such groupings rather than on individual pixels). For each pixel i an auto-exposure value of the pixel ($V_i$) may be compared to the auto-exposure value threshold (Th) at operation 606. As shown, this may continue for as long as there are still pixels (or pixel groupings) of the image frame that have not yet been analyzed (Not Done), and may end when all of the pixels of the image frame have been iterated through (Done). In certain examples, rather than iterating through all of the pixels of the image frame, a certain region of the image frame (e.g., a central region of the image frame such as a central 50% of the image frame, a central 80% of the image frame, etc.) may be accounted for while another region of the image frame (e.g., a peripheral region of the image frame such as an outer 50% of the image frame, an outer 20% of the image frame, etc.) may be ignored for purposes of auto-exposure management. In such examples, operation 504 may finish iterating (Done) when all the pixels of the region that is to be accounted for (e.g., the central region) have been iterated through. At operation 606, the comparison between the pixel auto-exposure value and the auto-exposure value threshold may be configured to provide one of two outcomes: (1) the pixel auto-exposure value may exceed the auto-exposure value threshold ($V_i$>Th); or (2) the pixel auto-exposure value might not exceed the auto-exposure value threshold ($V_i$<Th). It will be understood that, in the event that the pixel auto-exposure value is equal to the auto-exposure value threshold, the pixel auto-exposure value may be counted as exceeding or not exceeding the auto-exposure value threshold as may serve a particular implementation.

Pixels having auto-exposure values that exceed the auto-exposure value threshold may be identified to be in the signal region in operation 608. Conversely, pixels having auto-exposure values that do not exceed the auto-exposure value threshold may be identified to be in the background region in operation 610. Flow may then proceed from operation 608 or 610 back to operation 604 where the next pixel or group of pixels may be analyzed until the image frame (e.g., the entire image frame or a portion of the image frame) has been processed and the signal and background regions have been successfully identified.

While FIG. 6 shows one suitable way for identifying the signal region and the background region of an image frame, it will be understood that other ways of achieving the same or a similar outcome may also be employed in other implementations. For example, certain implementations may involve determining probabilities for each pixel (or pixel grouping) and identifying the pixels in the signal or background region based on their respective probabilities, or performing similar auto-exposure value threshold or probability comparisons on groupings of pixels (e.g., cells of a grid into which the pixels could be subdivided) rather than individual pixels. As another example, as illustrated above in relation to FIGS. 4A and 4B, a boundary may be identified around a signal region that either closely conforms to the signal region or that is a standard shape (e.g., a polygon such as a rectangle, a circle, etc.), and certain noisy pixels that might otherwise exceed the auto-exposure value threshold may thereby be identified as part of the background due to being outside the boundary.

Returning to FIG. 5, after the signal region is distinguished from the background region in operation 504, flow may proceed to operation 506. In operation 506, one or more auto-exposure data points such as a signal auto-exposure value ($V_S$), a signal auto-exposure target ($T_S$), a background auto-exposure value ($V_B$), a background auto-exposure target ($T_B$), and/or any other suitable auto-exposure data points (not explicitly shown in FIG. 5) may be determined. In certain implementations, each of these auto-exposure data points may be determined at this stage for every frame so that the needed data will be ready regardless of which branch is taken with respect to the three different cases that will be described below in relation to operations 514-518. In other implementations, operation 506 might not be performed at the stage in the process shown in FIG. 5, but, rather, auto-exposure data points may be determined on an as needed basis as flow moves to one branch of the diagram or another. In these types of implementations, apparatus 100 might not ultimately determine every auto-exposure data point for every image frame, but may instead just determine those data points that are actually to be used (e.g., the signal auto-exposure value and signal auto-exposure target for the signal-only case of operation 514, the background auto-exposure value and background auto-exposure target for the background-only case of operation 516, etc.).

Apparatus 100 may determine each auto-exposure data point in any suitable manner at operation 506 based on captured data associated with the image frame obtained at operation 502 and based on the signal and background regions identified at operation 504. For example, apparatus 100 may determine the signal auto-exposure value to be an average of the auto-exposure values (e.g., a mean, median, mode, or other suitable average) of the pixels identified (at operation 504) to be included within the signal region, and/or may determine the background auto-exposure value to be an average of the auto-exposure values (e.g., a mean, median, mode, or other suitable average) of the pixels identified (at operation 504) to be included within the background region. Similarly, apparatus 100 may determine the signal auto-exposure target to be an average auto-exposure target for the pixels identified (at operation 504) to be included within the signal region, and/or may determine the background auto-exposure target to be an average auto-exposure target for the pixels identified (at operation 504) to be included within the background region.

At operation 508 (which may be performed subsequent to, prior to, or concurrently with operation 506), apparatus 100 may determine a signal region size value(S) that, as will be described in more detail below, may be used to determine how the auto-exposure data points determined at operation 506 are used, processed, and/or combined to form a frame auto-exposure value and/or a frame auto-exposure target for the image frame. To this end, the signal region size value may be determined so as to represent a size of the signal region within the image frame in any suitable way. For example, the signal region size value may represent the size of the signal region by being set to an area of the signal region, a total number of pixels (or pixel groupings or cells) included in the signal region, a total percentage of pixels included in the signal region compared to the total number of pixels included in the image frame, a ratio of pixels included in the signal region to pixels included in the background region, or any other value that represents the size, significance, prominence, or other such characteristic of the signal region (e.g., with respect to the background region, with respect to the entire image frame, etc.) as may serve a particular implementation.

At operations 510 and 512, comparisons may be made between the signal region size value determined at operation 508 and an upper signal region size threshold (upper threshold $Th_U$) and between the signal region size value and a lower signal region size threshold (lower threshold $Th_L$). While operations 510 and 512 are illustrated in FIG. 5 as being performed in a particular order (e.g., operation 510 first, followed by operation 512), it will be understood that operations 510 and 512 may, in certain examples, be performed concurrently or in the opposite order (e.g., operation 512 first, followed by operation 510). Moreover, while both operations are included for the illustrative embodiment of flow diagram 500, it will be understood that only one threshold may be used and one of these operations may be performed for embodiments that implement only two of the three cases. For example, in an embodiment that implements only the signal-only case and the signal and background case (and not the background-only case), a single threshold used at operation 510 may suffice and operation 512 may be omitted (e.g., by flow proceeding straight to operation 518 when the signal region size value is determined to be less than the upper threshold at operation 510). Similarly, in an embodiment that implements only the background-only case and the signal and background case (and not the signal-only case), a single threshold used at operation 512 may suffice and operation 510 may be omitted (e.g., by flow proceeding straight from operation 508 to operation 512).

Based on the comparisons performed at operations 510 and/or 512, the flow may move to one of three operations (e.g., operation 514, 516, or 518) where one or more of the auto-exposure data points determined at operation 506 may be used by apparatus 100 as a basis for determining a frame auto-exposure value ($V_F$) and/or a frame auto-exposure target ($T_F$). More specifically, as shown at operation 510, if the signal region size value exceeds the upper signal region size threshold ($S>Th_U$), flow proceeds to the signal-only case implemented by operation 514 and described in more detail below in relation to FIG. 7. Conversely, if the signal region size value does not exceed the upper signal region size threshold ($S<Th_U$), flow proceeds to operation 512 where a comparison is made between the signal region size value and the lower signal region size threshold. At operation 512, if the signal region size value does not exceed the lower signal region size threshold ($S<Th_L$), flow proceeds to the background-only case implemented by operation 516 and described in more detail below in relation to FIG. 8. Conversely, if, at operation 512, the signal region size value exceeds the lower signal region size threshold ($S>Th_L$), flow proceeds to the signal and background case implemented by operation 518 and described in more detail below in relation to FIG. 9.

In the event that the signal region size value is equal to either the upper or lower signal region size thresholds, the signal region size value may be counted as exceeding or not exceeding the respective threshold, and flow may proceed in either direction as may best serve a particular implementation. Each of FIGS. 7-9 will now be described to illustrate different ways of determining frame auto-exposure values and frame auto-exposure targets for the different cases represented by operations 514-518.

Figure 7:
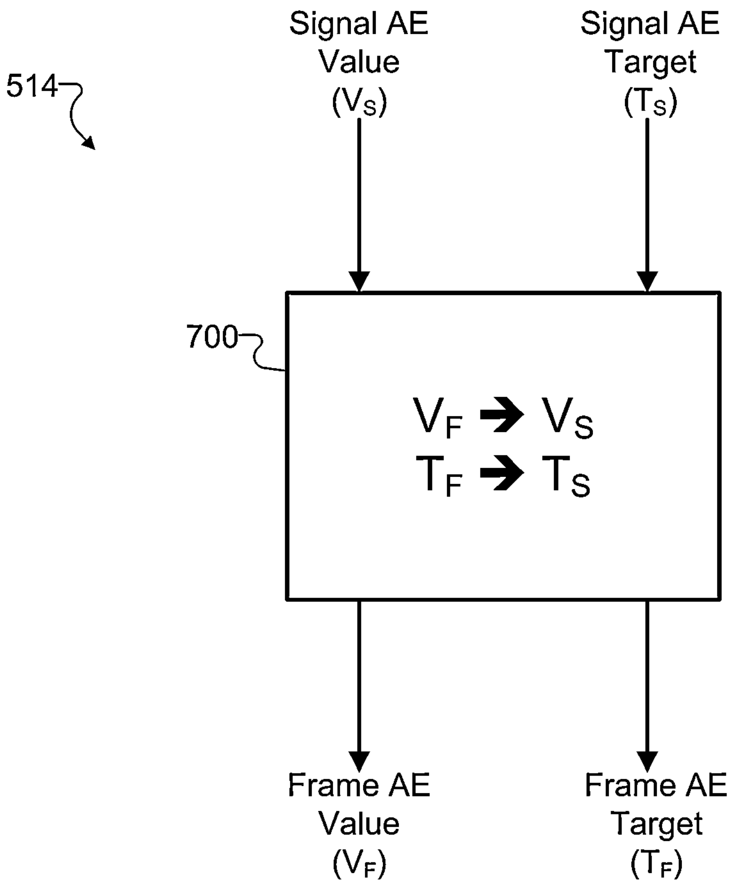
FIGS. 7-9 show illustrative ways of determining frame auto-exposure values and frame auto-exposure targets according to principles described herein.

FIG. 7 shows a manner in which the frame auto-exposure value and/or the frame auto-exposure target may be determined in operation 514 for the signal-only case. As mentioned above, flow may arrive at operation 514 when the signal region size value is determined to exceed the upper signal region size threshold. It is noted that, because the upper signal region size threshold is defined as a higher threshold than the lower signal region size threshold, the signal region size value will necessarily also exceed the lower signal region size threshold when flow arrives at operation 514. The signal-only case illustrated by FIG. 7 may occur when there is a relatively large signal area and a relatively small background area, such as when the signal area covers a relatively large number of pixels or a relatively large percentage of the overall image frame. In the examples described above relating to fluorescence-guided medical procedures, the signal-only case may occur, for instance, when a relatively large amount of fluorescing tissue is in view of the image capture system.

Whether apparatus 100 considers the size of the signal region size value to be large enough to proceed to the signal-only case of operation 514 may depend on the value of the upper signal region size threshold, which may be set at any level as may serve a particular implementation. For example, in one implementation, the upper signal region size threshold could be defined so as to only be exceeded when the signal region covers more than half of the image frame and is therefore larger than the background region. In another implementation, the upper signal region size threshold could be defined so as to be exceeded whenever the signal region covers at least 10%, at least 1%, or any other suitable portion of the image frame as may serve a particular implementation.

In FIG. 7, an illustrative operation 700 shows one possible way that operation 514 may be implemented. Specifically, operation 700 is shown to bring in two inputs: signal auto-exposure value ($V_S$) and signal auto-exposure target ($T_S$). Based on detecting that the signal region size value exceeds the upper signal region size threshold (the basis upon which flow has arrived at operation 514) and as shown by the assignments made in operation 700 (designated using assignment arrows), apparatus 100 may determine the frame auto-exposure value to correspond to the signal auto-exposure value ($V_F \rightarrow V_S$), and/or may determine the frame auto-exposure target to correspond to the signal auto-exposure target ($T_F \rightarrow T_S$).

In some implementations, determining a frame auto-exposure data point (e.g., the frame auto-exposure value or frame auto-exposure target) to correspond to a signal auto-exposure data point (e.g., the signal auto-exposure value or signal auto-exposure target) may involve setting the frame auto-exposure data point to be equal to the signal auto-exposure data point. For instance, the frame auto-exposure value may be set to equal the signal auto-exposure value, and the frame auto-exposure target may be set to equal the signal auto-exposure target. In other implementations, determining the frame auto-exposure data point to correspond to the signal auto-exposure data point may involve setting the frame auto-exposure data point to a version of the corresponding signal auto-exposure data point that has been scaled or otherwise modified, but that still represents the signal auto-exposure data point and not a background auto-exposure data point. For this reason, the case covered by operation 514 is referred to herein as the signal-only case because the frame auto-exposure data points are determined based only on corresponding signal auto-exposure data points and not background auto-exposure data points.

Figure 8:
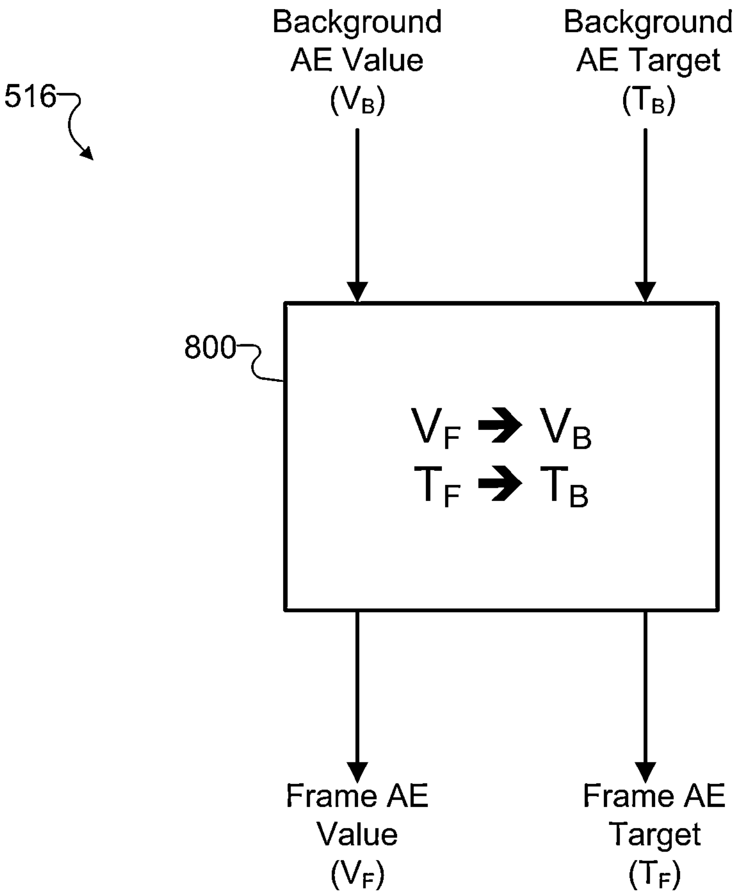

FIG. 8 shows a manner in which the frame auto-exposure value and/or the frame auto-exposure target may be determined in operation 516 for the background-only case. As mentioned above, flow may arrive at operation 516 when the signal region size value is determined to not exceed the lower signal region size threshold. It is noted that, because the lower signal region size threshold is defined as a lower threshold than the upper signal region size threshold, the signal region size value will necessarily also not exceed the upper signal region size threshold when flow arrives at operation 516. The background-only case illustrated by FIG. 8 may occur when there is a relatively small signal area and a relatively large background area, such as when the signal area covers a relatively small number of pixels or a relatively small percentage of the overall image frame. In the examples described above relating to fluorescence-guided medical procedures, the background-only case may occur, for example, when a relatively small amount of fluorescing tissue is in view of the image capture system or if there is no fluorescing tissue at all.

Whether apparatus 100 considers the size of the signal region size value to be small enough to proceed to the background-only case of operation 516 may depend on the value of the lower signal region size threshold, which may be set at any level as may serve a particular implementation. For example, in one implementation, the lower signal region size threshold could be defined so as to only not be exceeded when the signal region covers less than half of the image frame and is therefore smaller than the background region. In another implementation, the lower signal region size threshold could be defined so as to not be exceeded when the signal region covers less than 10%, less than 1%, or less than any other suitable portion of the image frame as may serve a particular implementation.

In FIG. 8, an illustrative operation 800 shows one possible way that operation 516 may be implemented. Specifically, operation 800 is shown to bring in two inputs: background auto-exposure value ($V_B$) and background auto-exposure target ($T_B$). Based on the detecting that the signal region size value does not exceed the lower signal region size threshold (the basis upon which flow has arrived at operation 516) and as shown by the assignments made in operation 800 (designated using assignment arrows), apparatus 100 may determine the frame auto-exposure value to correspond to the background auto-exposure value ($V_F \rightarrow V_B$), and/or may determine the frame auto-exposure target to correspond to the background auto-exposure target ($T_F \rightarrow T_B$).

In some implementations, determining a frame auto-exposure data point (e.g., the frame auto-exposure value or frame auto-exposure target) to correspond to a background auto-exposure data point (e.g., the background auto-exposure value or background auto-exposure target) may involve setting the frame auto-exposure data point to be equal to the background auto-exposure data point. For instance, the frame auto-exposure value may be set to equal the background auto-exposure value and the frame auto-exposure target may be set to equal the background auto-exposure target. In other implementations, determining the frame auto-exposure data point to correspond to the background auto-exposure data point may involve setting the frame auto-exposure data point to a version of the corresponding background auto-exposure data point that has been scaled or otherwise modified, but that still represents the background auto-exposure data point and not a signal auto-exposure data point. For this reason, the case covered by operation 516 is referred to herein as the background-only case because the frame auto-exposure data points are determined based only on corresponding background auto-exposure data points and not signal auto-exposure data points.

As described and illustrated above in relation to FIG. 5, the signal region size value may, in certain scenarios, be detected to be between the lower and upper signal region size thresholds (e.g., to exceed the lower signal region size threshold while not exceeding the upper signal region size threshold). For these scenarios, apparatus 100 may be configured to manage auto-exposure in a manner that is somewhere in between the signal-only case of operation 514 and the background-only case of operation 516 as these have been described above.

Figure 9:
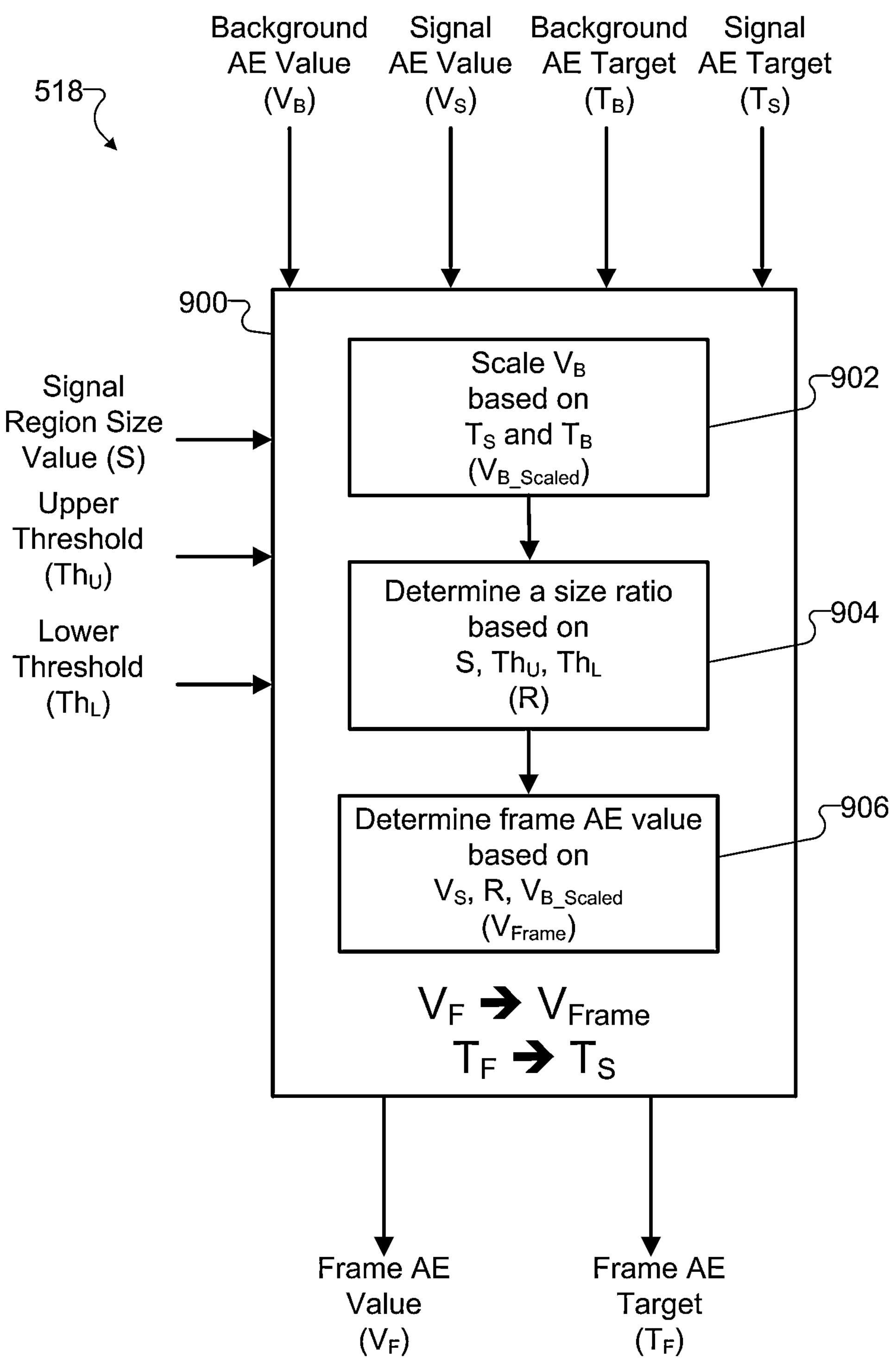

To illustrate, FIG. 9 shows a manner in which the frame auto-exposure value and/or the frame auto-exposure target may be determined in operation 518 for the signal and background case. As mentioned above, flow may arrive at operation 518 when the signal region size value is determined to exceed the lower signal region size threshold and to not exceed the upper signal region size threshold (e.g., to fall somewhere between the two thresholds). The signal and background case illustrated by FIG. 9 may occur, for example, when there is a moderately sized signal area and a moderately sized background area such that it would not be optimal for auto-exposure management to treat the entire image frame as if it were either completely signal or completely background. In the examples described above relating to fluorescence-guided medical procedures, the signal and background case may occur, for example, when a moderate amount of fluorescing tissue is in view of the image capture system. As described above, the upper and lower signal region size threshold may be set and defined to any suitable values at which the signal region size thresholds are different from one another and the upper signal region size threshold is the greater of the two.

In FIG. 9, an illustrative operation 900 shows one possible way that operation 518 may be implemented. As shown, operation 900 may allow for a balancing of both signal- and background-related considerations. More specifically, operation 900 is shown to bring in various inputs including signal auto-exposure data points (e.g., signal auto-exposure value ($V_S$) and signal auto-exposure target ($T_S$)), background auto-exposure data points (e.g., background auto-exposure value ($V_B$) and background auto-exposure target ($T_B$)), the signal region size value (S), and signal region size thresholds (e.g., the upper signal region size threshold ($Th_U$) and the lower signal region size threshold ($Th_L$)). Based on detecting that the signal region size value exceeds the lower signal region size threshold and does not exceed the upper signal region size threshold (the basis upon which flow has arrived at operation 518), apparatus 100 may determine the frame auto-exposure value ($V_F$) based on the signal auto-exposure value and the background auto-exposure value. This may be done, for example, by performing various operations 902-906 described in more detail below. As shown, apparatus 100 may also determine the frame auto-exposure target ($T_F$) to correspond to the signal auto-exposure target in a similar way as described above for the signal-only case. In other examples, apparatus 100 may determine the frame auto-exposure target in another manner (e.g., to result in a frame auto-exposure target between the signal and background auto-exposure targets).

At operation 902, apparatus 100 may scale the background auto-exposure value based on the signal auto-exposure target and the background auto-exposure target to determine a scaled background auto-exposure value ($V_{B\_SCALED}$). For example, in various implementations, the background auto-exposure value may be scaled proportionally to the signal auto-exposure target, scaled inversely proportionally to the background auto-exposure target, or scaled by a ratio of the signal auto-exposure target and the background auto-exposure target. As one specific example, Eq. 1 shows a particular way the scaling may be performed:

$$V_{B\_SCALED} = V_B * \frac{T_S}{T_B} \qquad \text{(Eq. 1)}$$

At operation 904, apparatus 100 may determine a size ratio (R) based on the signal region size value, the upper signal region size threshold, and the lower signal region size threshold. For example, in various implementations, the size ratio may be determined based on a ratio of the upper and lower signal region size thresholds, a ratio of 1) the difference of the signal region size value and the upper signal region size threshold and 2) the difference of the upper signal region size threshold and the lower signal region size threshold, or another ratio representative of how the signal region size value relates to each of the upper and lower signal region size thresholds. As one specific example, Eq. 2 shows a particular way the size ratio may be determined:

$$R = \min\left(1.0, \max\left(0.0, \frac{S - Th_U}{Th_U - Th_L}\right)\right) \qquad \text{(Eq. 2)}$$

At operation 906, apparatus 100 may determine a raw frame auto-exposure value ($V_{FRAME}$) based on the signal auto-exposure value, the size ratio, and the scaled background auto-exposure value. For example, in various implementations, the raw frame auto-exposure value may be determined to be an average (e.g., a mean average) of the signal auto-exposure value and the scaled background auto-exposure value, or scaled/modified versions thereof. In some instances, the signal auto-exposure value may be multiplied by the size ratio while the scaled background auto-exposure value may be multiplied by a difference between 1 and the size ratio (1–R). As one specific example, Eq. 3 shows a particular way the raw frame auto-exposure value may be determined:

$$V_{FRAME} = V_S * R + V_{B\_SCALED} * (1 - R) \qquad \text{(Eq. 3)}$$

As shown by the assignment arrows at the bottom of operation 900, after operations 902-906 have been performed, the frame auto-exposure value may be determined to correspond to the raw frame auto-exposure value ($V_F \rightarrow V_{FRAME}$), and/or the frame auto-exposure target may be determined to correspond to the signal auto-exposure target ($T_F \rightarrow T_S$), as was mentioned above. As previously described in relation to FIGS. 7 and 8, the frame auto-exposure data points may be determined to correspond to corresponding auto-exposure data points (e.g., the raw frame auto-exposure value and the signal auto-exposure target in this example) by setting the frame auto-exposure data points to be equal to the corresponding auto-exposure data points, whereas, in other implementations, the frame auto-exposure data points may be determined to correspond to scaled or otherwise modified versions of their corresponding auto-exposure data points. Regardless, the case covered by operation 518 is referred to herein as the signal and background case because the frame auto-exposure data points are determined based on both signal and background auto-exposure data points, rather than on either one of these alone.

Returning to FIG. 5, once the frame auto-exposure value and/or frame auto-exposure target have been determined by one of operations 514-518, flow may arrive at operation 520. In operation 520, auto-exposure parameters of the image capture system may be adjusted or otherwise updated (e.g., determined to not need adjustment and therefore maintained at their current setpoints) based on the frame auto-exposure value and/or the frame auto-exposure target.

Figure 10:
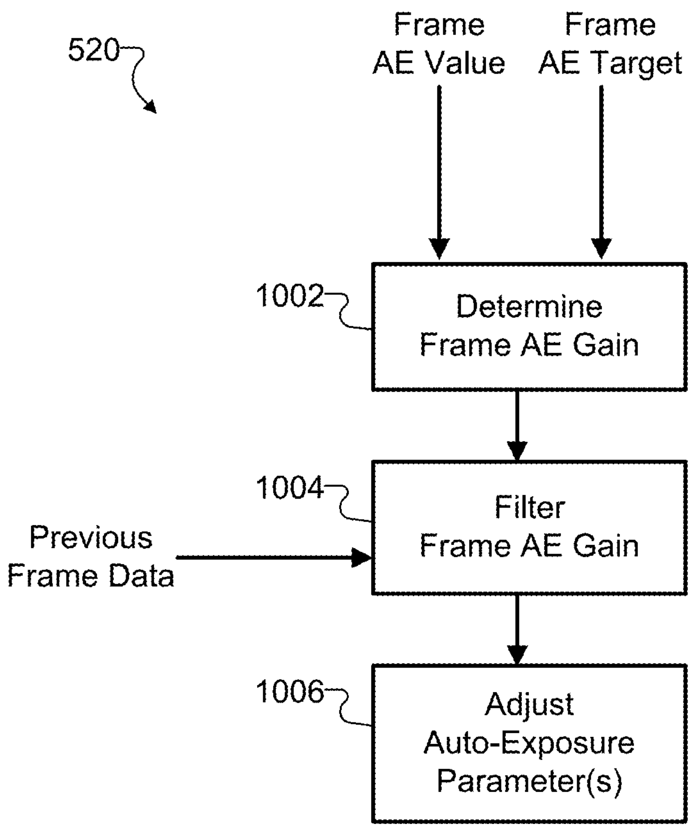
FIG. 10 shows an illustrative flow diagram for adjusting an auto-exposure parameter according to principles described herein.

The process of adjusting the auto-exposure parameters at operation 520 may involve several operations not explicitly shown in FIG. 5. To illustrate, FIG. 10 shows an illustrative flow diagram for adjusting an auto-exposure parameter at operation 520.

As shown, an operation 1002 takes the frame auto-exposure value and frame auto-exposure target as inputs and uses them as a basis for determining a frame auto-exposure gain. For example, the frame auto-exposure gain may be determined to correspond to a ratio of the frame auto-exposure target to the frame auto-exposure value. In this way, if the frame auto-exposure value is already equal to the frame auto-exposure target (e.g., such that no further adjustment is needed to align to the target), the frame auto-exposure gain may be set to a gain of 1, so that the system will neither try to boost nor attenuate the auto-exposure values for a subsequent frame that the image capture system captures. Conversely, if the frame auto-exposure target is different from the frame auto-exposure value, the frame auto-exposure gain may be set to correspond to a value less than or greater than 1 to cause the system to either boost or attenuate the auto-exposure values for the subsequent frame in an attempt to make the auto-exposure values more closely match a desired auto-exposure target.

At operation 1004, the frame auto-exposure gain may be taken as an input along with other data (e.g., other frame auto-exposure gains) determined for previous image frames in the image frame sequence. Based on these inputs, operation 1004 applies filtering to ensure that the auto-exposure gain does not change more quickly than desired and to thereby ensure that the brightness of image frames presented to the user maintain a consistent brightness and change gradually. The filtering performed at operation 1004 may be performed using a smoothing filter such as a temporal infinite impulse response (IIR) filter or another such digital or analog filter as may serve a particular implementation.

At operation 1006, the filtered auto-exposure gain may be used as a basis for adjusting one or more auto-exposure parameters of the image capture system (e.g., for use by the image capture device or the fluorescence illumination source in capturing additional image frames). For example, as described above, adjusted auto-exposure parameters may include an exposure time parameter, a shutter aperture parameter, a luminance gain parameter, or the like. For image capture systems in which the illumination of the scene is largely or completely controlled by the image capture system (e.g., an image capture system including an endoscopic image capture device described above, an image capture system including a flash or other illumination source, etc.), adjusted auto-exposure parameters may further include an illumination intensity parameter, an illumination duration parameter, or the like.

Adjustments to the auto-exposure parameters of the image capture system may cause the image capture system to expose subsequent image frames in various different ways. For example, by adjusting the exposure time parameter, a shutter speed may be adjusted for a shutter included in the image capture system. For instance, the shutter may be held open for a longer period of time (e.g., to thereby increase the amount of exposure time of an image sensor) or for a shorter period of time (e.g., to thereby decrease the amount of exposure time for the image sensor). As another example, by adjusting the shutter aperture parameter, an aperture of the shutter may be adjusted to open more widely (e.g., to thereby increase the amount of light exposed to the image sensor) or less widely (e.g., to thereby decrease the amount of light exposed to the image sensor). As yet another example, by adjusting the luminance gain parameter, a sensitivity (e.g., an ISO sensitivity) may be increased or decreased to amplify or attenuate the illuminance as captured by the image capture system. For implementations in which the image capture system controls the illumination of the scene, the illumination intensity and/or illumination duration parameters may be adjusted to increase the intensity and duration of the light used to illuminate the scene being captured, thereby also affecting how much light the image sensor is exposed to.

Based on any adjustments to the auto-exposure parameters (and/or based on maintaining the auto-exposure parameters at their current levels when appropriate), apparatus 100 may successfully manage auto-exposure for image frames being captured by the image capture system, and subsequent image frames may be captured with desirable auto-exposure properties so as to have an attractive and beneficial appearance when presented to users.

As has been described, apparatus 100, method 200, and/or system 300 may each be associated in certain examples with a computer-assisted medical system used to perform a medical procedure (e.g., a fluorescence-guided medical procedure) on a body. To illustrate, FIG. 11 shows an illustrative computer-assisted medical system 1100 that may be used to perform various types of medical procedures including surgical and/or non-surgical procedures.

Figure 11:
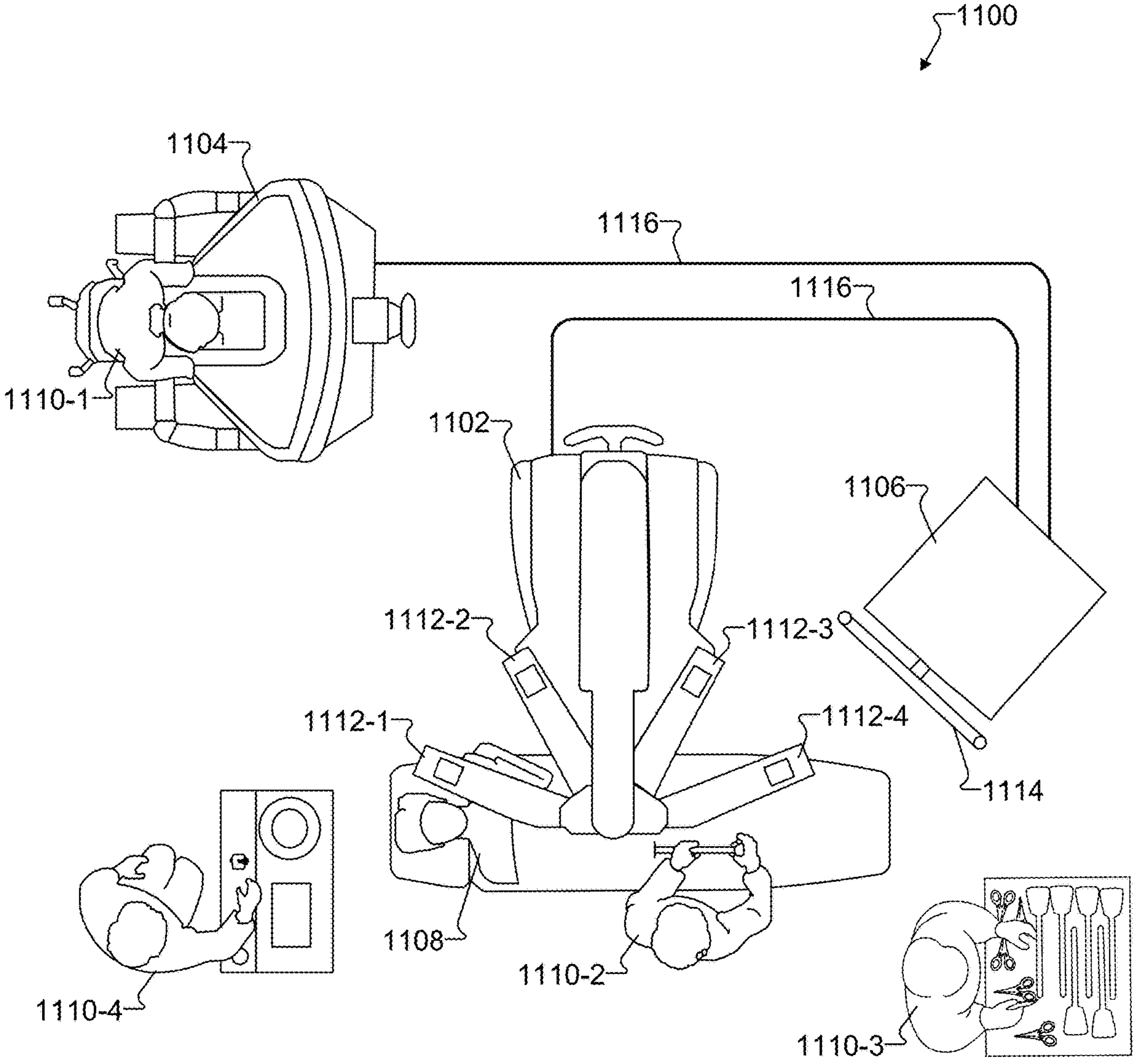
FIG. 11 shows an illustrative computer-assisted medical system according to principles described herein.

As shown, computer-assisted medical system 1100 may include a manipulator assembly 1102 (a manipulator cart is shown in FIG. 11), a user control apparatus 1104, and an auxiliary apparatus 1106, all of which are communicatively coupled to each other. Computer-assisted medical system 1100 may be utilized by a medical team to perform a computer-assisted medical procedure or other similar operation on a body of a patient 1108 or on any other body as may serve a particular implementation. As shown, the medical team may include a first user 1110-1 (such as a surgeon for a surgical procedure), a second user 1110-2 (such as a patient-side assistant), a third user 1110-3 (such as another assistant, a nurse, a trainee, etc.), and a fourth user 1110-4 (such as an anesthesiologist for a surgical procedure), all of whom may be collectively referred to as "users 1110," and each of whom may control, interact with, or otherwise be a user of computer-assisted medical system 1100. More, fewer, or alternative users may be present during a medical procedure as may serve a particular implementation. For example, team composition for different medical procedures, or for non-medical procedures, may differ and include users with different roles.

While FIG. 11 illustrates an ongoing minimally invasive medical procedure such as a minimally invasive surgical procedure, it will be understood that computer-assisted medical system 1100 may similarly be used to perform open medical procedures or other types of operations. For example, operations such as exploratory imaging operations, mock medical procedures used for training purposes, and/or other operations may also be performed.

As shown in FIG. 11, manipulator assembly 1102 may include one or more manipulator arms 1112 (e.g., manipulator arms 1112-1 through 1112-4) to which one or more instruments may be coupled. The instruments may be used for a computer-assisted medical procedure on patient 1108 (e.g., in a surgical example, by being at least partially inserted into patient 1108 and manipulated within patient 1108). While manipulator assembly 1102 is depicted and described herein as including four manipulator arms 1112, it will be recognized that manipulator assembly 1102 may include a single manipulator arm 1112 or any other number of manipulator arms as may serve a particular implementation. While the example of FIG. 11 illustrates manipulator arms 1112 as being robotic manipulator arms, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 1112 shown in FIG. 11.

During the medical operation, user control apparatus 1104 may be configured to facilitate teleoperational control by user 1110-1 of manipulator arms 1112 and instruments attached to manipulator arms 1112. To this end, user control apparatus 1104 may provide user 1110-1 with imagery of an operational area associated with patient 1108 as captured by an imaging device. To facilitate control of instruments, user control apparatus 1104 may include a set of master controls. These master controls may be manipulated by user 1110-1 to control movement of the manipulator arms 1112 or any instruments coupled to manipulator arms 1112.

Auxiliary apparatus 1106 may include one or more computing devices configured to perform auxiliary functions in support of the medical procedure, such as providing insufflation, electrocautery energy, illumination or other energy for imaging devices, image processing, or coordinating components of computer-assisted medical system 1100. In some examples, auxiliary apparatus 1106 may be configured with a display monitor 1114 configured to display one or more user interfaces, or graphical or textual information in support of the medical procedure. In some instances, display monitor 1114 may be implemented by a touchscreen display and provide user input functionality. Augmented content provided by a region-based augmentation system may be similar, or differ from, content associated with display monitor 1114 or one or more display devices in the operation area (not shown).

As will be described in more detail below, apparatus 100 may be implemented within or may operate in conjunction with computer-assisted medical system 1100. For instance, in certain implementations, apparatus 100 may be implemented by computing resources included within an instrument (e.g., an endoscopic or other imaging instrument) attached to one of manipulator arms 1112, or by computing resources associated with manipulator assembly 1102, user control apparatus 1104, auxiliary apparatus 1106, or another system component not explicitly shown in FIG. 11.

Manipulator assembly 1102, user control apparatus 1104, and auxiliary apparatus 1106 may be communicatively coupled one to another in any suitable manner. For example, as shown in FIG. 11, manipulator assembly 1102, user control apparatus 1104, and auxiliary apparatus 1106 may be communicatively coupled by way of control lines 1116, which may represent any wired or wireless communication link as may serve a particular implementation. To this end, manipulator assembly 1102, user control apparatus 1104, and auxiliary apparatus 1106 may each include one or more wired or wireless communication interfaces, such as one or more local area network interfaces, Wi-Fi network interfaces, cellular interfaces, and so forth.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 12:
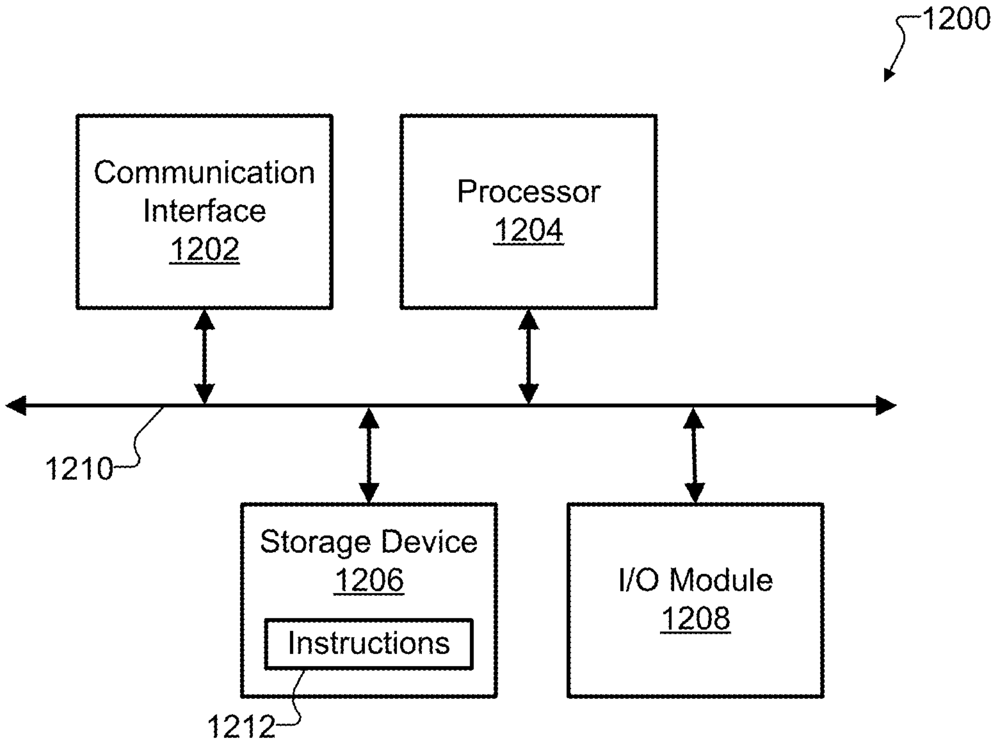
FIG. 12 shows an illustrative computing system according to principles described herein.

FIG. 12 shows an illustrative computing system 1200 that may be specifically configured to perform one or more of the processes described herein. For example, computing system 1200 may include or implement (or partially implement) an auto-exposure management apparatus such as apparatus 100, an auto-exposure management system such as system 300, or any other computing systems or devices described herein.

As shown in FIG. 12, computing system 1200 may include a communication interface 1202, a processor 1204, a storage device 1206, and an input/output ("I/O") module 1208 communicatively connected via a communication infrastructure 1210. While an illustrative computing system 1200 is shown in FIG. 12, the components illustrated in FIG. 12 are not intended to be limiting. Additional or alternative components may be used in other embodiments. Components of computing system 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1206. For example, data representative of one or more executable applications 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1200. For example, one or more applications 1212 residing within storage device 1206 may be configured to direct processor 1204 to perform one or more processes or functions associated with processor 104 of apparatus 100. Likewise, memory 102 of apparatus 100 may be implemented by or within storage device 1206.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:

one or more processors; and memory storing executable instructions that, when executed by the one or more processors, cause the apparatus to:

identify, within an image frame captured by an image capture system, a signal region of the image frame and a background region of the image frame;

determine one or more of a signal auto-exposure value of the signal region or a background auto-exposure value of the background region; and adjust, based on one or more of the signal auto-exposure value or the background auto-exposure value, one or more auto-exposure parameters used by the image capture system to capture an additional image frame;

wherein the identifying the signal region and the background region includes:

identifying pixels of the image frame that have auto-exposure values that exceed an auto-exposure value threshold to be included within the signal region, the auto-exposure value threshold determined by linearly scaling a baseline threshold with a frame auto-exposure gain associated with the image frame, and identifying pixels of the image frame that have auto-exposure values that do not exceed the auto-exposure value threshold to be included within the background region.

2. The apparatus of claim 1, wherein the determining the one or more of the signal auto-exposure value or the background auto-exposure value comprises one or more of:

determining the signal auto-exposure value to be an average of the auto-exposure values of the pixels identified to be included within the signal region; or determining the background auto-exposure value to be an average of the auto-exposure values of the pixels identified to be included within the background region.

3. The apparatus of claim 1, wherein the one or more auto-exposure parameters include one or more of:

an exposure time parameter;

a shutter aperture parameter;

an illumination intensity parameter; or a luminance gain parameter.

4. The apparatus of claim 1, wherein:

the image frame depicts fluorescence content against a darkened background, the fluorescence content generated by a fluorescence imaging agent that fluoresces when illuminated by a fluorescence illumination source;

the signal region identified within the image frame corresponds to the fluorescence content; and the background region identified within the image frame corresponds to the darkened background.

5. The apparatus of claim 4, wherein:

the image capture system includes an endoscopic image capture device configured to capture the image frame as part of an image frame sequence that depicts a view of a body undergoing a fluorescence-guided medical procedure; and the endoscopic image capture device captures the image frame while operating in a fluorescence imaging mode that facilitates viewing tissue of the body to which the fluorescence imaging agent has been applied.

6. The apparatus of claim 1, wherein:

the instructions, when executed by the one or more processors, cause the apparatus to determine, based on one or more of the signal auto-exposure value or the background auto-exposure value, a frame auto-exposure value; and the adjusting the one or more auto-exposure parameters is based on the frame auto-exposure value.

7. The apparatus of claim 6, wherein:

the instructions, when executed by the one or more processors, cause the apparatus to:

determine, based on one or more of a signal auto-exposure target or a background auto-exposure target, a frame auto-exposure target, determine, based on the frame auto-exposure value and the frame auto-exposure target, a frame auto-exposure gain; and the adjusting the one or more auto-exposure parameters includes adjusting the one or more auto-exposure parameters based on the frame auto-exposure gain.

8. The apparatus of claim 7, wherein:

the instructions, when executed by the one or more processors, cause the apparatus to filter, using a smoothing filter and based on one or more frame auto-exposure gains associated with one or more image frames in an image frame sequence that includes the image frame, the frame auto-exposure gain; and the adjusting the one or more auto-exposure parameters is based on the filtered frame auto-exposure gain.

9. The apparatus of claim 6, wherein:

the instructions, when executed by the one or more processors, cause the apparatus to determine a signal region size value representative of a size of the signal region within the image frame; and the determining the frame auto-exposure value is further based on the signal region size value.

10. The apparatus of claim 9, wherein:

the instructions, when executed by the one or more processors, cause the apparatus to:

determine one or more of a signal auto-exposure target of the signal region or a background auto-exposure target of the background region, and determine, based on the signal region size value and one or more of the signal auto-exposure target or the background auto-exposure target, a frame auto-exposure target; and wherein the adjusting the one or more auto-exposure parameters is further based on the frame auto-exposure target.

11. The apparatus of claim 10, wherein:

the instructions, when executed by the one or more processors, cause the apparatus to detect that the signal region size value exceeds a signal region size threshold;

the determining the frame auto-exposure value includes determining, based on the detecting that the signal region size value exceeds the signal region size threshold, the frame auto-exposure value to correspond to the signal auto-exposure value; and the determining the frame auto-exposure target includes determining, based on the detecting that the signal region size value exceeds the signal region size threshold, the frame auto-exposure target to correspond to the signal auto-exposure target.

12. The apparatus of claim 10, wherein:

the instructions, when executed by the one or more processors, cause the apparatus to detect that the signal region size value does not exceed a signal region size threshold;

the determining the frame auto-exposure value includes determining, based on the detecting that the signal region size value does not exceed the signal region size threshold, the frame auto-exposure value to correspond to the background auto-exposure value; and the determining the frame auto-exposure target includes determining, based on the detecting that the signal region size value does not exceed the signal region size threshold, the frame auto-exposure target to correspond to the background auto-exposure target.

13. The apparatus of claim 10, wherein:

the instructions, when executed by the one or more processors, cause the apparatus to detect that the signal region size value exceeds a lower signal region size threshold and does not exceed an upper signal region size threshold;

the determining the frame auto-exposure value includes determining, based on the detecting that the signal region size value exceeds the lower signal region size threshold and does not exceed the upper signal region size threshold, the frame auto-exposure value based on the signal auto-exposure value and the background auto-exposure value; and the determining the frame auto-exposure target includes determining, based on the detecting that the signal region size value exceeds the lower signal region size threshold and does not exceed the upper signal region size threshold, the frame auto-exposure target to correspond to the signal auto-exposure target.

14. The apparatus of claim 13, wherein the determining the frame auto-exposure value based on the signal auto-exposure value and the background auto-exposure value includes:

scaling the background auto-exposure value based on the signal auto-exposure target and the background auto-exposure target;

determining a size ratio based on the signal region size value, the upper signal region size threshold, and the lower signal region size threshold; and determining the frame auto-exposure value based on the signal auto-exposure value, the size ratio, and the scaled background auto-exposure value.

15. A system comprising:

a fluorescence illumination source configured to illuminate tissue within a body undergoing a fluorescence-guided medical procedure, wherein a portion of the tissue includes a fluorescence imaging agent that fluoresces when illuminated by the fluorescence illumination source;

an image capture device configured to capture an image frame sequence that includes an image frame depicting a view of the body as the tissue is illuminated by the fluorescence illumination source; and one or more processors configured to:

identify, within the image frame captured by the image capture device, a signal region of the image frame associated with the portion of the tissue that includes the fluorescence imaging agent and a background region of the image frame associated with a portion of the tissue that does not include the fluorescence imaging agent;

determine one or more of a signal auto-exposure value of the signal region or a background auto-exposure value of the background region; and adjust, based on one or more of the signal auto-exposure value or the background auto-exposure value, one or more auto-exposure parameters used by the image capture device or the fluorescence illumination source to capture an additional image frame of the image frame sequence;

wherein the identifying the signal region and the background region includes:

identifying pixels of the image frame that have auto-exposure values that exceed an auto-exposure value threshold to be included within the signal region, the auto-exposure value threshold determined by linearly scaling a baseline threshold with a frame auto-exposure gain associated with the image frame, and identifying pixels of the image frame that have auto-exposure values that do not exceed the auto-exposure value threshold to be included within the background region.

16. The system of claim 15, wherein:

the one or more processors are further configured to determine, based on one or more of the signal auto-exposure value or the background auto-exposure value, a frame auto-exposure value; and the adjusting the one or more auto-exposure parameters is based on the frame auto-exposure value.

17. The system of claim 16, wherein the one or more processors are configured to:

determine one or more of a signal auto-exposure target of the signal region or a background auto-exposure target of the background region;

determine a signal region size value representative of a size of the signal region within the image frame; and determine, based on the signal region size value and one or more of the signal auto-exposure target or the background auto-exposure target, a frame auto-exposure target;

wherein:

the determining the frame auto-exposure value is further based on the signal region size value, and the adjusting the one or more auto-exposure parameters is further based on the frame auto-exposure target.

18. The system of claim 17, wherein:

the one or more processors are configured to detect that the signal region size value exceeds a signal region size threshold;

the determining the frame auto-exposure value includes determining, based on the detecting that the signal region size value exceeds the signal region size threshold, the frame auto-exposure value to correspond to the signal auto-exposure value; and the determining the frame auto-exposure target includes determining, based on the detecting that the signal region size value exceeds the signal region size threshold, the frame auto-exposure target to correspond to the signal auto-exposure target.

19. A method comprising:

identifying, within an image frame captured by an image capture system, a signal region of the image frame and a background region of the image frame;

determining one or more of a signal auto-exposure value of the signal region or a background auto-exposure value of the background region; and adjusting, based on one or more of the signal auto-exposure value or the background auto-exposure value, one or more auto-exposure parameters used by the image capture system to capture an additional image frame;

wherein the identifying the signal region and the background region includes:

identifying pixels of the image frame that have auto-exposure values that exceed an auto-exposure value threshold to be included within the signal region, the auto-exposure value threshold determined by linearly scaling a baseline threshold with a frame auto-exposure gain associated with the image frame, and identifying pixels of the image frame that have auto-exposure values that do not exceed the auto-exposure value threshold to be included within the background region.

* * * * *